US005723583A

United States Patent [19]
Seed et al.

[11] Patent Number: 5,723,583
[45] Date of Patent: Mar. 3, 1998

[54] ANTIBODY CONTAINING SIALYL LEWIS X DETERMINANTS

[75] Inventors: Brian Seed; Gerd Walz, both of Boston, Mass.

[73] Assignee: The General Hospital Corporation, Boston, Mass.

[21] Appl. No.: 480,036

[22] Filed: Jun. 7, 1995

Related U.S. Application Data

[63] Continuation of Ser. No. 618,314, Nov. 23, 1990, abandoned.

[51] Int. Cl.$^6$ ............................................. C07K 16/00
[52] U.S. Cl. ............................. 530/387.3; 530/391.1; 424/133.1; 514/23
[58] Field of Search ........................... 530/387.3, 391.1, 530/395; 424/133.1; 514/23

[56] References Cited

U.S. PATENT DOCUMENTS

| | | | |
|---|---|---|---|
| 4,184,917 | 1/1980 | Dorner et al. | 435/68.1 |
| 4,344,938 | 8/1982 | Sedlacek et al. | 424/130.1 |
| 4,752,569 | 6/1988 | Terasaki et al. | 435/7.23 |
| 4,816,567 | 3/1989 | Cabilly et al. | 530/387.3 |
| 4,840,793 | 6/1989 | Todd, III et al. | 424/153.1 |
| 4,851,511 | 7/1989 | Hakomori et al. | 530/387.5 |
| 4,923,980 | 5/1990 | Blomberg | 536/55.2 |
| 5,079,353 | 1/1992 | Ratcliffe et al. | 536/53 |
| 5,143,712 | 9/1992 | Brandley et al. | 424/1.73 |
| 5,211,936 | 5/1993 | Brandley et al. | 424/1.73 |

FOREIGN PATENT DOCUMENTS

| | | |
|---|---|---|
| 0 146 090 | 6/1985 | European Pat. Off. . |
| 0 218 257 | 4/1987 | European Pat. Off. . |
| 0 251 304 | 1/1988 | European Pat. Off. . |
| 0 314 863 | 5/1989 | European Pat. Off. . |
| 0 319 253 | 6/1989 | European Pat. Off. . |
| 0 323 802 | 7/1989 | European Pat. Off. . |
| 1 550 914 | 8/1979 | United Kingdom . |
| WO89/08711 | 9/1989 | WIPO . |
| WO90/05539 | 5/1990 | WIPO . |
| WO90/05786 | 5/1990 | WIPO . |
| WO90/13300 | 11/1990 | WIPO . |
| WO91/16900 | 11/1991 | WIPO . |
| US91/08605 | 1/1992 | WIPO . |
| WO92/02527 | 2/1992 | WIPO . |

OTHER PUBLICATIONS

Goochee et al. in Frontiers in Bioprocessing II, ed. Todd et al. pp. 199–240, 1992.

Springer, "Adhesion receptors of the immune system", Nature 346: 425–434 (Aug. 1990).

M. Laurie Phillips et al., ELAM–1 Mediates Cell Adhesion by Recognition of a Carbohydrate Ligand, Sialyl–Le$^x$ Science, vol. 250, pp. 1130–1132; 28 Aug. 1990.

Gerd Walz et al., Recognition by ELAM–1 of the Sialyl–Le Determinant on Myeloid and Tumor Cells; Science, vol. 250, pp. 1132–1135; 30 Aug. 1990.

Aruffo et al., The EMBO Journal 6(11):3313–3316, 1987.

Seed et al., Proc. Natl. Acad. Sci. USA 84:3365–3369, 1987.
Aruffo et al., Proc. Natl. Acad. Sci USA 84:8573–8577, 1987.
Aruffo et al., Cell, 61:1303–1313, 1990.
Bevilacqua et al., Science 243:1160, 1989.
Seed, Nature 329:840, 1987.
Lowe et al., Cell 63:475–484, 1990.
Johnson et al., Biochemical Society Transactions, p. 396, 1987, vol. 15(3).
Okada et al., Clinica Chimica Acta 86(1978) 159–167.
Kijima–Suda et al., Cancer Research 46:858–862, 1986.
Bowen et al., The Journal of Cell Biology 109:421–427, 1989.
Rice et al., Science 246:1303, 1989.
Stoolman, Cell 56:907–910, 1989.
Dobrina et al., Immunology 67:502–508, 1989.
Streeter et al., The Journal of Cell Biology, 107:1853–1862, 1988.
Streeter et al., Nature 331:41, 1988.
Messadi et al., The Journal of Immunology 139(5):1557–1562, 1987.
Munro et al., Cytokine Interactions in Pathological Processes (8858–8863) p. A1821, No. 8862.
Pober et al., The Journal of Immunology 136(5):1680–1686, 1986.
Klein et al., Proc. Natl. Acad. Sci. USA 86:8972–8976, 1989.
Cotran et al., J. Exp. Med. 164:661–666, 1986.
Vedder et al., J. Clin. Invest. 81:939–944, 1988.
Jutila et al., Transplantation 48:727–731, 1989.
Simpson et al., J. Clin. Invest. 81:624–629, 1988.
Luscinskas et al., The Journal of Immunology 142:2257–2263, 1989.
Paclic et al., Carbohydrate Research 190:1–11, 1989.
Masson et al., Clinica Chimica Acta, 187:199–206, 1990.
Fukushima et al., Cancer Research 44:5279–5285, 1984.
Fujiwara et al., Journal of Immunological Methods 112:77–83, 1988.
Herrero–Zabaleta et al., Bull. Cancer 74:387–396, 1987.
Le Pendu et al., Biochimie 70:1613–1617, 1988.
Mollicone et al., Blood, 71(4):1113–1119, 1988.

(List continued on next page.)

*Primary Examiner*—Stephen Walsh
*Assistant Examiner*—Karen E. Brown
*Attorney, Agent, or Firm*—Clark & Elbing LLP

[57] ABSTRACT

Disclosed is a method of inhibiting the binding of a cell bearing a cell adhesion protein to a molecule or cell bearing a carbohydrate determinant specific for the cell adhesion molecule. The method involves contacting the cell adhesion protein-bearing cell with an inhibitor molecule bearing the carbohydrate determinant. Also disclosed is a method of inhibiting the binding of the first member of a specific binding pair to the second member of the specific binding pair, involving contacting the first member with an antibody which is specific for the first member and which is covalently bonded to a carbohydrate moiety which interferes with the antibody's ability to fix complement and bind an $F_c$ receptor. The methods of the invention may be used, for example, to reduce inflammation.

5 Claims, 10 Drawing Sheets

OTHER PUBLICATIONS

Kuriyama et al., Biochimica et Biophysica Acta 662:220–225, 1981.

Baker et al., Cancer Research 47:2763–2766, 1987.

Arnaout et al., Journal of Cellular Physiology 137:305–309, 1988.

Hession et al., Proc. Natl. Acad. Sci. USA 87:1673–1677, 1990.

Ball et al., The Journal of Immunology 130(6):2937, 1983.

Hansson et al., The Journal of Biological Chemistry, 260(16):9388–9392, 1985.

Macher et al., The Journal of Biological Chemistry 263(21):10186–10191, 1986.

Stanley et al., Journal of Biological Chemistry, vol. 263, No. 23, Issued Aug. 15, 1988, pp. 11374–11381.

Ghetie et al., Molecular Immunology, vol. 23, No. 4, Issued 1986, pp. 377–384.

Fukuda et al., Journal of Biological Chemistry, vol. 259, No. 17, Issued Sep. 10, 1984, pp. 10925–10935.

```
    AAGCTTACCACCATGGACTGGACCTGGAGGTTCCTCTTCTTTGTGGTGGCAGCAGCTACA
1   ---------+---------+---------+---------+---------+---------+  60
    TTCGAATGGTGGTACCTGACCTGGACCTCCAAGGAGAAGAAACACCACCGTCGTCGATGT

K  L  T  T  M  D  W  T  W  R  F  L  F  F  V  V  A  A  A  T  -

GGTGTCCAGTCCCAGGTGCAGCTGGTGCAGTCTGGGGCTGAGGTGAAGAAGCCTGGGTCC
61  ---------+---------+---------+---------+---------+---------+ 120
    CCACAGGTCAGGGTCCACGTCGACCACGTCAGACCCCGACTCCACTTCTTCGGACCCAGG

G  V  Q  S  Q  V  Q  L  V  Q  S  G  A  E  V  K  K  P  G  S  -

TCGGTGAAGGTCTCCTGCAAGGCTTCTGGAGGCACCTTCAGCAGCTATGCTATCAGCTGG
121 ---------+---------+---------+---------+---------+---------+ 180
    AGCCACTTCCAGAGGACGTTCCGAAGACCTCCGTGGAAGTCGTCGATACGATAGTCGACC

S  V  K  V  S  C  K  A  S  G  G  T  F  S  S  Y  A  I  S  W  -

GTGCGACAGGCCCCTGGACAAGGGCTTGAGTGGATGGGAGGGATCATCCCTATCTTTGGT
181 ---------+---------+---------+---------+---------+---------+ 240
    CACGCTGTCCGGGGACCTGTTCCCGAACTCACCTACCCTCCCTAGTAGGGATAGAAACCA

V  R  Q  A  P  G  Q  G  L  E  W  M  G  G  I  I  P  I  F  G  -

ACAGCAAACTACGCACAGAAGTTCCAGGGCAGAGTCACGATTACCGCGGACGAATCCACG
241 ---------+---------+---------+---------+---------+---------+ 300
    TGTCGTTTGATGCGTGTCTTCAAGGTCCCGTCTCAGTGCTAATGGCGCCTGCTTAGGTGC

T  A  N  Y  A  Q  K  F  Q  G  R  V  T  I  T  A  D  E  S  T  -

AGCACAGCCTACATGGAGCTGAGCAGCCTGAGATCTGAGGACACGGCCGTGTATTACTGT
301 ---------+---------+---------+---------+---------+---------+ 360
    TCGTGTCGGATGTACCTCGACTCGTCGGACTCTAGACTCCTGTGCCGGCACATAATGACA

S  T  A  Y  M  E  L  S  S  L  R  S  E  D  T  A  V  Y  Y  C  -

GCGAGAGATAATGGAGCGTATTGTAGTGGTGGTAGCTGCTACTCGGGCTGGTTCGACCCC
361 ---------+---------+---------+---------+---------+---------+ 420
    CGCTCTCTATTACCTCGCATAACATCACCACCATCGACGATGAGCCCGACCAAGCTGGGG

A  R  D  N  G  A  Y  C  S  G  G  S  C  Y  S  G  W  F  D  P  -

TGGGGCCAGGGAACCCTGGTCACCGTCTCTTCAGGTGAGTACTGAATTCTAGCTTTCTGG
421 ---------+---------+---------+---------+---------+---------+ 480
    ACCCCGGTCCCTTGGGACCAGTGGCAGAGAAGTCCACTCATGACTTAAGATCGAAAGACC

```
     GGCAGGCCAGGCCTGACCTTGGCTTTGGGGCAGGGAGGGGGCTAAGGTGAGGCAGGTGGC
481  ---------+---------+---------+---------+---------+---------+ 540
     CCGTCCGGTCCGGACTGGAACCGAAACCCCGTCCCTCCCCCGATTCCACTCCGTCCACCG

GCCAGCAGGTGCACACCCAATGCCCATGAGCCCAGACACTGGACGCTGAACCTCGCGGAC
541  ---------+---------+---------+---------+---------+---------+ 600
     CGGTCGTCCACGTGTGGGTTACGGGTACTCGGGTCTGTGACCTGCGACTTGGAGCGCCTG

AGTTAAGAACCCAGGGGCCTCTGCGCCTGGGCCCAGCTCTGTCCCACACCGCGGTCACAT
601  ---------+---------+---------+---------+---------+---------+ 660
     TCAATTCTTGGGTCCCCGGAGACGCGGACCCGGGTCGAGACAGGGTGTGGCGCCAGTGTA

GGCACCACCTCTCTTGCAGCCTCCACCAAGGGCCCATCGGTCTTCCCCCTGGCACCCTCC
661  ---------+---------+---------+---------+---------+---------+ 720
     CCGTGGTGGAGAGAACGTCGGAGGTGGTTCCCGGGTAGCCAGAAGGGGGACCGTGGGAGG

A  S  T  K  G  P  S  V  F  P  L  A  P  S   -

TCCAAGAGCACCTCTGGGGGCACAGCGGCCCTGGGCTGCCTGGTCAAGGACTACTTCCCC
721  ---------+---------+---------+---------+---------+---------+ 780
     AGGTTCTCGTGGAGACCCCCGTGTCGCCGGGACCCGACGGACCAGTTCCTGATGAAGGGG

S  K  S  T  S  G  G  T  A  A  L  G  C  L  V  K  D  Y  F  P  -

GAACCGGTGACGGTGTCGTGGAACTCAGGCGCCCTGACCAGCGGCGTGCACACCTTCCCG
781  ---------+---------+---------+---------+---------+---------+ 840
     CTTGGCCACTGCCACAGCACCTTGAGTCCGCGGGACTGGTCGCCGCACGTGTGGAAGGGC

E  P  V  T  V  S  W  N  S  G  A  L  T  S  G  V  H  T  F  P  -

GCTGTCCTACAGTCCTCAGGACTCTACTCCCTCAGCAGCGTGGTGACCGTGCCCTCCAGC
841  ---------+---------+---------+---------+---------+---------+ 900
     CGACAGGATGTCAGGAGTCCTGAGATGAGGGAGTCGTCGCACCACTGGCACGGGAGGTCG

A  V  L  Q  S  S  G  L  Y  S  L  S  S  V  V  T  V  P  S  S  -

AGCTTGGGCACCCAGACCTACATCTGCAACGTGAATCACAAGCCCAGCAACACCAAGGTG
901  ---------+---------+---------+---------+---------+---------+ 960
     TCGAACCCGTGGGTCTGGATGTAGACGTTGCACTTAGTGTTCGGGTCGTTGTGGTTCCAC

S  L  G  T  Q  T  Y  I  C  N  V  N  H  K  P  S  N  T  K  V  -

GACAAGAAAGTTGGTGAGAGGCCAGCACAGGGAGGGAGGGTGTCTGCTGGAAGCAGGCTC
961  ---------+---------+---------+---------+---------+---------+ 1020
     CTGTTCTTTCAACCACTCTCCGGTCGTGTCCCTCCCTCCCACAGACGACCTTCGTCCGAG

```
     AGCGCTCCTGCCTGGACGCATCCCGGCTATGCAGCCCCAGTCCAGGGCAGCAAGGCAGGC
1021 ---------+---------+---------+---------+---------+---------+ 1080
     TCGCGAGGACGGACCTGCGTAGGGCCGATACGTCGGGGTCAGGTCCCGTCGTTCCGTCCG

CCCGTCTGCCTCTTCACCCGGAGCCTCTGCCCGCCCCACTCATGCTCAGGGAGAGGGTCT
1081 ---------+---------+---------+---------+---------+---------+ 1140
     GGGCAGACGGAGAAGTGGGCCTCGGAGACGGGCGGGGTGAGTACGAGTCCCTCTCCCAGA

TCTGGCTTTTTCCCAGGCTCTGGGCAGGCACAGGCTAGGTGCCCCTAACCCAGGCCCTGC
1141 ---------+---------+---------+---------+---------+---------+ 1200
     AGACCGAAAAAGGGTCCGAGACCCGTCCGTGTCCGATCCACGGGGATTGGGTCCGGGACG

ACACAAAGGGGCAGGTGCTGGGCTCAGACCTGCCAAGAGCCATATCCGGGAGGACCCTGC
1201 ---------+---------+---------+---------+---------+---------+ 1260
     TGTGTTTCCCCGTCCACGACCCGAGTCTGGACGGTTCTCGGTATAGGCCCTCCTGGGACG

CCCTGACCTAAGCCCACCCCAAAGGCCAAACTCTCCACTCCCTCAGCTCGGACACCTTCT
1261 ---------+---------+---------+---------+---------+---------+ 1320
     GGGACTGGATTCGGGTGGGGTTTCCGGTTTGAGAGGTGAGGGAGTCGAGCCTGTGGAAGA

CTCCTCCCAGATTCCAGTAACTCCCAATCTTCTCTCTGCAGAGCCCAAATCTTGTGACAA
1321 ---------+---------+---------+---------+---------+---------+ 1380
     GAGGAGGGTCTAAGGTCATTGAGGGTTAGAAGAGAGACGTCTCGGGTTTAGAACACTGTT
                                          E  P  K  S  C  D  K  -

AACTCACACATGCCCACCGTGCCCAGGTAAGCCAGCCCAGGCCTCGCCCTCCAGCTCAAG
1381 ---------+---------+---------+---------+---------+---------+ 1440
     TTGAGTGTGTACGGGTGGCACGGGTCCATTCGGTCGGGTCCGGAGCGGGAGGTCGAGTTC
      T  H  T  C  P  P  C  P

GCGGGACAGGTGCCCTAGAGTAGCCTGCATCCAGGGACAGGCCCCAGCCGGGTGCTGACA
1441 ---------+---------+---------+---------+---------+---------+ 1500
     CGCCCTGTCCACGGGATCTCATCGGACGTAGGTCCCTGTCCGGGGTCGGCCCACGACTGT

CGTCCACCTCCATCTCTTCCTCAGCACCTGAACTCCTGGGGGGACCGTCAGTCTTCCTCT
1501 ---------+---------+---------+---------+---------+---------+ 1560
     GCAGGTGGAGGTAGAGAAGGAGTCGTGGACTTGAGGACCCCCCTGGCAGTCAGAAGGAGA
                    A  P  E  L  L  G  G  P  S  V  F  L  F  -
```

Fig. 1-3

```
          TCCCCCCAAAACCCAAGGACACCCTCATGATCTCCCGGACCCCTGAGGTCACATGCGTGG
1561      ------------+---------+---------+---------+---------+---------+  1620
          AGGGGGGTTTTGGGTTCCTGTGGGAGTACTAGAGGGCCTGGGGACTCCAGTGTACGCACC

P  P  K  P  K  D  T  L  M  I  S  R  T  P  E  V  T  C  V  V -

TGGTGGACGTGAGCCACGAAGACCCTGAGGTCAAGTTCAACTGGTACGTGGACGGCGTGG
1621      ------------+---------+---------+---------+---------+---------+  1680
          ACCACCTGCACTCGGTGCTTCTGGGACTCCAGTTCAAGTTGACCATGCACCTGCCGCACC
                                          N        S
            V  D  V  S  H  E  D  P  E  V  K  F  N  W  Y  V  D  G  V  E -

AGGTGCATAATGCCAAGACAAAGCCGCGGGAGGAGCAGTACAACAGCACGTACCGGGTGG
1681      ------------+---------+---------+---------+---------+---------+  1740
          TCCACGTATTACGGTTCTGTTTCGGCGCCCTCCTCGTCATGTTGTCGTGCATGGCCCACC
                   N                              N     S
            V  H  N  A  K  T  K  P  R  E  E  Q  Y  N  S  T  Y  R  V  V -

TCAGCGTCCTCACCGTCCTGCACCAGGACTGGCTGAATGGCAAGGAGTACAAGTGCAAGG
1741      ------------+---------+---------+---------+---------+---------+  1800
          AGTCGCAGGAGTGGCAGGACGTGGTCCTGACCGACTTACCGTTCCTCATGTTCACGTTCC
                                                                   N
            S  V  L  T  V  L  H  Q  D  W  L  N  G  K  E  Y  K  C  K  V -

TCTCCAACAAAGCCCTCCCAGCCCCCATCGAGAAAACCATCTCCAAAGCCAAAGGTGGGA
1801      ------------+---------+---------+---------+---------+---------+  1860
          AGAGGTTGTTTCGGGAGGGTCGGGGGTAGCTCTTTTGGTAGAGGTTTCGGTTTCCACCCT
                 N
            S  N  K  A  L  P  A  P  I  E  K  T  I  S  K  A  K

CCCGTGGGGTGCGAGGGCCACATGGACAGAGGCCGGCTCGGCCCACCCTCTGCCCTGAGA
1861      ------------+---------+---------+---------+---------+---------+  1920
          GGGCACCCCACGCTCCCGGTGTACCTGTCTCCGGCCGAGCCGGGTGGGAGACGGGACTCT

GTGACCGCTGTACCAACCTCTGTCCTACAGGGCAGCCCCGAGAACCACAGGTGTACACCC
1921      ------------+---------+---------+---------+---------+---------+  1980
          CACTGGCGACATGGTTGGAGACAGGATGTCCCGTCGGGGCTCTTGGTGTCCACATGTGGG

G  Q  P  R  E  P  Q  V  Y  T -

TGCCCCCATCCCGGGATGAGCTGACCAAGAACCAGGTCAGCCTGACCTGCCTGGTCAAAG
1981      ------------+---------+---------+---------+---------+---------+  2040
          ACGGGGGTAGGGCCCTACTCGACTGGTTCTTGGTCCAGTCGGACTGGACGGACCAGTTTC

```
      GCTTCTATCCCAGCGACATCGCCGTGGAGTGGGAGAGCAATGGGCAGCCGGAGAACAACT
2041  ---------+---------+---------+---------+---------+---------+ 2100
      CGAAGATAGGGTCGCTGTAGCGGCACCTCACCCTCTCGTTACCCGTCGGCCTCTTGTTGA

F   Y   P   S   D   I   A   V   E   W   E   S   N   G   Q   P   E   N   N   Y -

ACAAGACCACGCCTCCCGTGCTGGACTCCGACGGCTCCTTCTTCCTCTACAGCAAGCTCA
2101  ---------+---------+---------+---------+---------+---------+ 2160
      TGTTCTGGTGCGGAGGGCACGACCTGAGGCTGCCGAGGAAGAAGGAGATGTCGTTCGAGT

K   T   T   P   P   V   L   D   S   D   G   S   F   F   L   Y   S   K   L   T -

CCGTGGACAAGAGCAGGTGGCAGCAGGGGAACGTCTTCTCATGCTCCGTGATGCATGAGG
2161  ---------+---------+---------+---------+---------+---------+ 2220
      GGCACCTGTTCTCGTCCACCGTCGTCCCCTTGCAGAAGAGTACGAGGCACTACGTACTCC

V   D   K   S   R   W   Q   Q   G   N   V   F   S   C   S   V   M   H   E   A -

CTCTGCACAACCACTACACGCAGAAGAGCCTCTCCCTGTCTCCGGGTAAATGAGTGCGAC
2221  ---------+---------+---------+---------+---------+---------+ 2280
      GAGACGTGTTGGTGATGTGCGTCTTCTCGGAGAGGGACAGAGGCCCATTTACTCACGCTG

L   H   N   H   Y   T   Q   K   S   L   S   L   S   P   G   K   *

GGCCGGC
2281  -------
      CCGGCCG
```

Fig. 1-5

| ADHESIVENESS | SCORE 1-5 |
|---|---|
| GRANULOCYTES | +++++ |
| HL-60 | ++++ |
| THP1 | ++++ |
| WIDR | ++ |
| U937 | (+) |
| HSB-2 | + |
Fig. 4
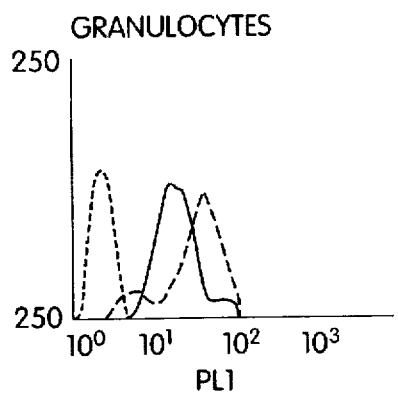
Fig. 5A
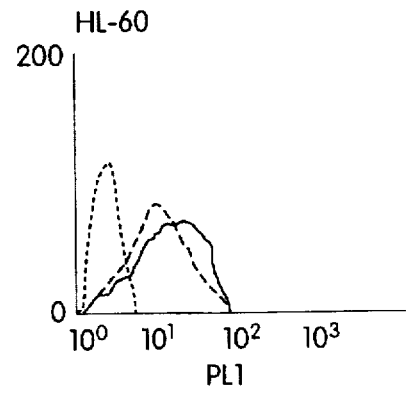
Fig. 5B
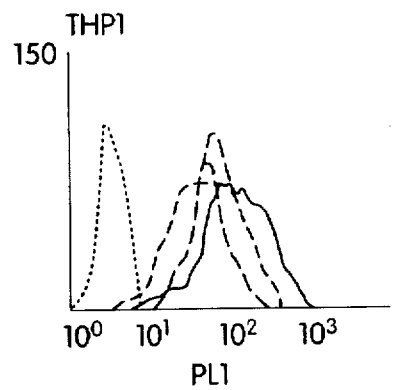
Fig. 5C
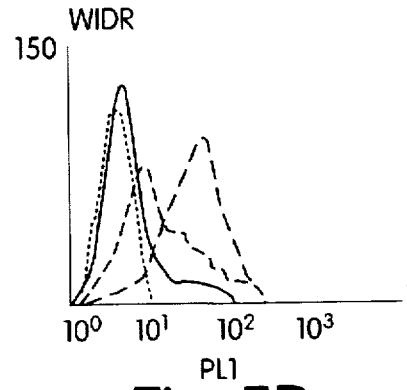
Fig. 5D
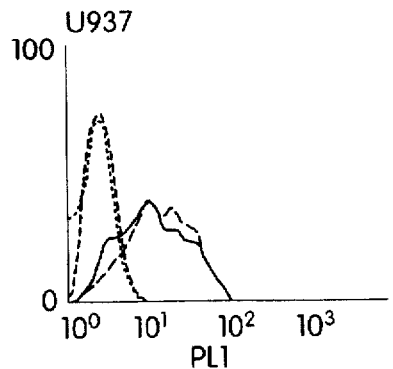
Fig. 5E
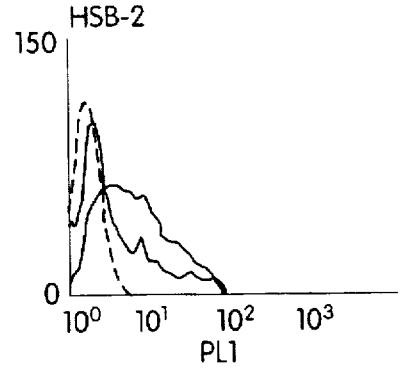
Fig. 5F

ANTIBODY CONTAINING SIALYL LEWIS X DETERMINANTS

This is a continuation of application Ser. No. 07/618,314, filed Nov. 23, 1990, now abandoned.

BACKGROUND OF THE INVENTION

This invention relates to therapeutic interference with interactions between cell adhesion proteins and their carbohydrate ligands.

ELAM-1 is an integral membrane adhesion protein. It possesses an extracellular domain including an N-terminal lectin-related segment, an epidermal growth factor related repeat, and multiple complement regulatory protein motifs (Bevilacqua et al., *Science* 243: 1160, 1989; Stoolman et al., *Cell* 56: 907, 1989). ELAM-1 is specifically expressed on the surface of endothelial cells activated by the cytokines IL-1 and tumor necrosis factor (TNF) (Bevilacqua et al., *Proc. Natl. Acad. Sci. USA* 84: 9238, 1987), or the peptide hormone Substance P (Matis et al., *J. Invest. Dermatol.* 94: 492, 1990). It mediates adhesion of myeloid cells (e.g., neutrophilic granulocytes) to cytokine-activated endothelial cells (Bevilacqua et al., *Proc. Natl. Acad. Sci USA* 84: 9238, 1987). It has been suggested that ELAM-1 is involved in the regulation of inflammatory and immunological events at the interface of the blood and the blood vessel wall (Bevilacqua et al., *Science* 243: 1160, 1989).

SUMMARY OF THE INVENTION

In general, the invention features a method of inhibiting the binding of a cell bearing a cell adhesion protein to a molecule or cell bearing a carbohydrate determinant specific for the cell adhesion molecule. The method involves contacting the cell adhesion protein-bearing cell with an inhibitor molecule bearing the carbohydrate determinant.

In preferred embodiments, the cell adhesion protein is a selectin, such as ELAM-1; the carbohydrate determinant is sialyl-Le$^x$; the sialyl-Le$^x$ determinant may be either N-linked or O-linked; the inhibitor molecule contains multiple sialyl-Le$^x$ determinants; the inhibitor molecule is a protein, preferably, $\alpha_1$-acid glycoprotein or an antibody, preferably, IgG1; the inhibitor molecule includes one or more of the N-linked glycan addition sites of $\alpha_1$-acid glycoprotein; and the inhibitor molecule is soluble.

In a related aspect, the invention features a method of reducing inflammation in a human patient involving administering to the patient a therapeutically-effective amount of an organic molecule bearing a sialyl-Le$^x$ determinant.

In preferred embodiments, the organic molecule contains multiple sialyl-Le$^x$ determinants; the sialyl-Le$^x$ determinant is either N-linked or O-linked; the organic molecule is a protein, preferably, $\alpha_1$-acid glycoprotein or an antibody, preferably, IgG1; and the organic molecule is soluble.

In another related aspect, the invention features a method of identifying an inhibitor molecule which blocks an interaction between an ELAM-1-bearing cell and a second cell or protein. The method involves contacting the ELAM-1-bearing cell with a candidate inhibitor molecule and with the second cell or protein, allowing an affinity complex between the ELAM-1-bearing cell and the second cell or protein to form, and identifying the inhibitor molecule as one which decreases formation of the affinity complex. Preferably, the second cell or protein bears a sialyl-Le$^x$ determinant.

In yet another related aspect, the invention features a method of inhibiting the binding of the first member of a specific binding pair to the second member of the specific binding pair, involving contacting the first member with an antibody which is specific for the first member and which is covalently bonded to a carbohydrate moiety which interferes with the antibody's ability to fix complement and bind an $F_c$ receptor.

In preferred embodiments, the first member is a protein and the second member is also a protein; the antibody is covalently bonded to multiple carbohydrate moieties; and the carbohydrate moiety is a sialyl-Le$^x$ determinant; the sialyl-Le$^x$ determinant is either N-linked or O-linked; and the antibody includes one or more of the N-linked glycan addition sites of $\alpha_1$-acid glycoprotein.

In another aspect, the invention features a cell-free organic molecule to which there is covalently bonded a carbohydrate determinant specific for a cell adhesion protein.

In preferred embodiments, the cell adhesion protein is a selectin, preferably, ELAM-1; the carbohydrate determinant is sialyl-Le$^x$; the sialyl-Le$^x$ is either N-linked or O-linked; the organic molecule is a protein, preferably, $\alpha_1$-acid glycoprotein or an antibody, preferably, IgG1; the presence of the carbohydrate determinant on the antibody interferes with the antibody's ability to fix complement and bind an $F_c$ receptor; the organic molecule includes one or more of the N-linked glycan addition sites of $\alpha_1$-acid glycoprotein; and the organic molecule bears multiple carbohydrate determinants.

The invention further features purified nucleic acid encoding an antibody containing sites for the attachment of a carbohydrate determinant which is specific for a cell adhesion protein; a vector including such nucleic acid; and a recombinant cell including such a vector.

Finally, the invention features a method of making a carrier molecule to which a carbohydrate specific for a cell adhesion protein is covalently bonded involving contacting the carrier molecule with an enzyme capable of attaching to the protein the carbohydrate determinant.

In preferred embodiments, the contacting occurs in a living cell; the cell is a eukaryotic, and preferably, a mammalian cell; the cell is a recombinant cell containing DNA encoding the enzyme; and the enzyme is an $\alpha(1,3)$ fucosyltransferase.

By "cell adhesion protein" is meant a protein, present at some point in its in vivo existence on the cell surface, which mediates a specific interaction with a protein (e.g., a protein bearing a carbohydrate ligand) on the surface of a second cell. By "carbohydrate determinant" is meant a moiety containing one or more carbohydrate groups which is present on a cell surface (at some point in its in vivo existence) and which interacts in a specific manner with a protein, e.g., a cell adhesion protein, e.g., on the surface of a second cell. By "selectin" is meant a member of a family of cellular adhesion molecules that are characterized structurally by the presence of a lectin-like domain, an epidermal growth factor-like domain, a series of cysteine-rich repeats, a transmembrane domain and a short cytoplasmic tail. By "inflammation" is meant a pathologic process consisting of cytologic and histologic reactions that occur in the affected blood vessels and adjacent tissues in response to an injury or abnormal stimulation caused by a physical, chemical, or biologic agent. By "specific binding pair" is meant any pair of molecules, including a first and second member, which have a specific affinity for each other. Examples of specific binding pairs include receptors and ligands, e.g., cell adhesion molecules and their carbohydrate ligands. By "purified nucleic acid" is meant nucleic acid which is separated from other sequences with which it is naturally associated. By "N-linked" is meant bonded to the amide nitrogen of an asparagine residue of a protein. By "O-linked" is meant bonded to the hydroxyl-group oxygen of a serine, threonine, or hydroxylysine residue of a protein.

DESCRIPTION OF THE PREFERRED EMBODIMENTS

The drawings will first briefly be described.

Drawings FIGS. 1-1–1-5 (SEQ ID NO:1) shows the sequence of IgG1 and mutations designed to create N-linked glycan addition sites.

FIG. 4 is a graph showing the degree of binding of a series of mammalian cell lines to an ELAM-1-IgG1 fusion protein;

Figure 6:
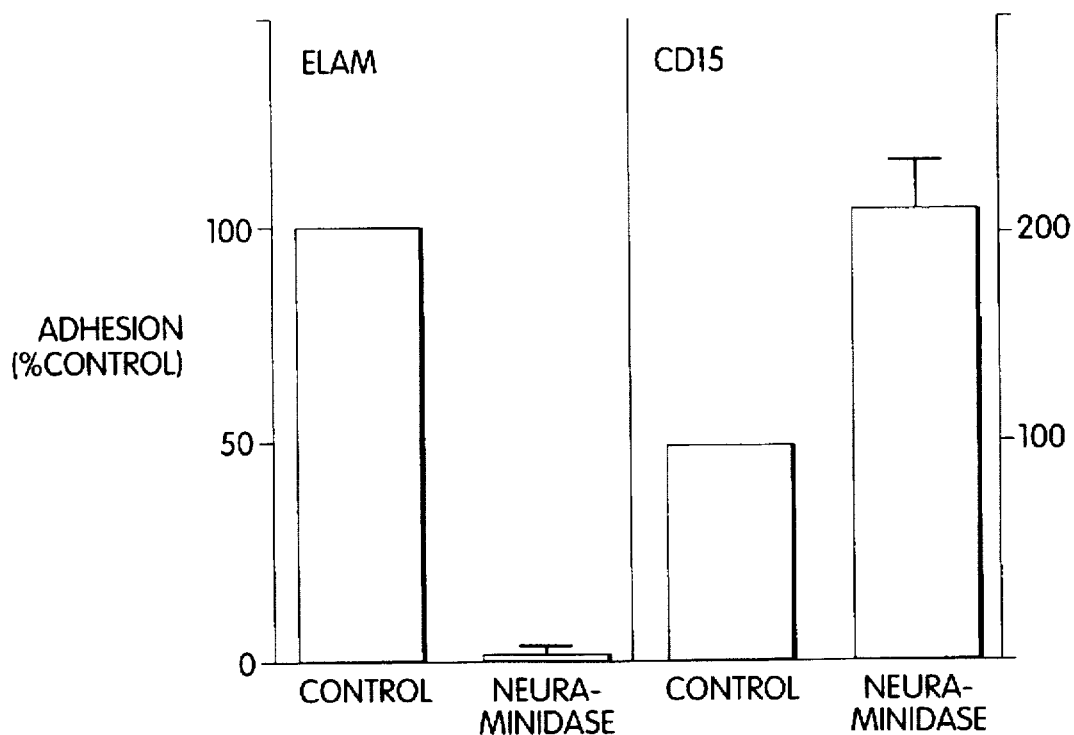
Figure 7:
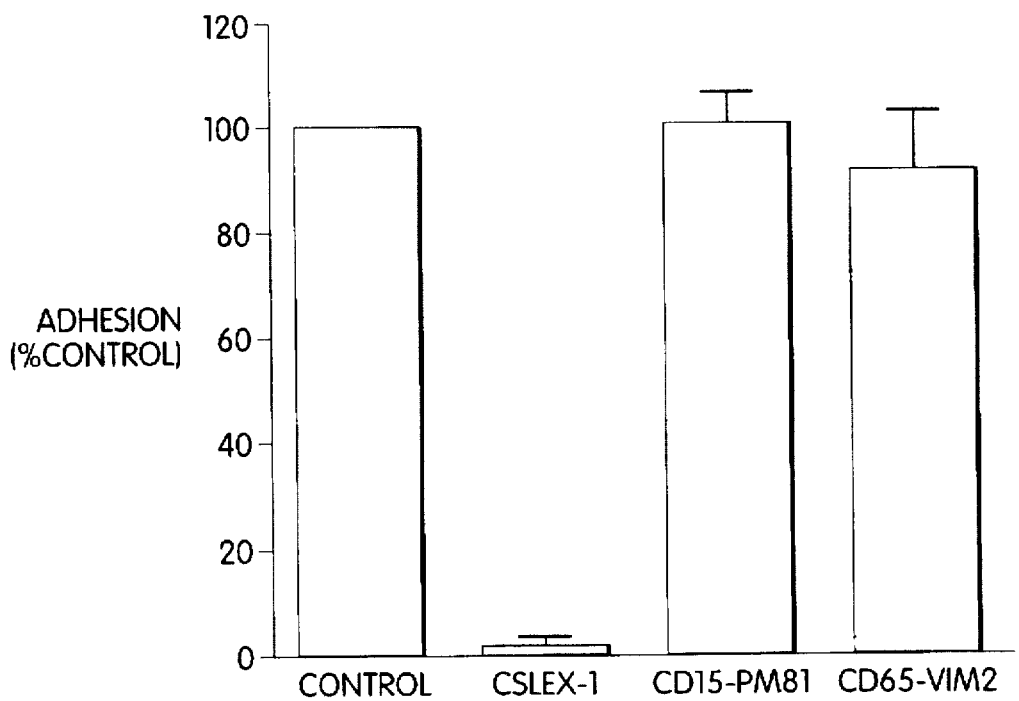
Figure 8:
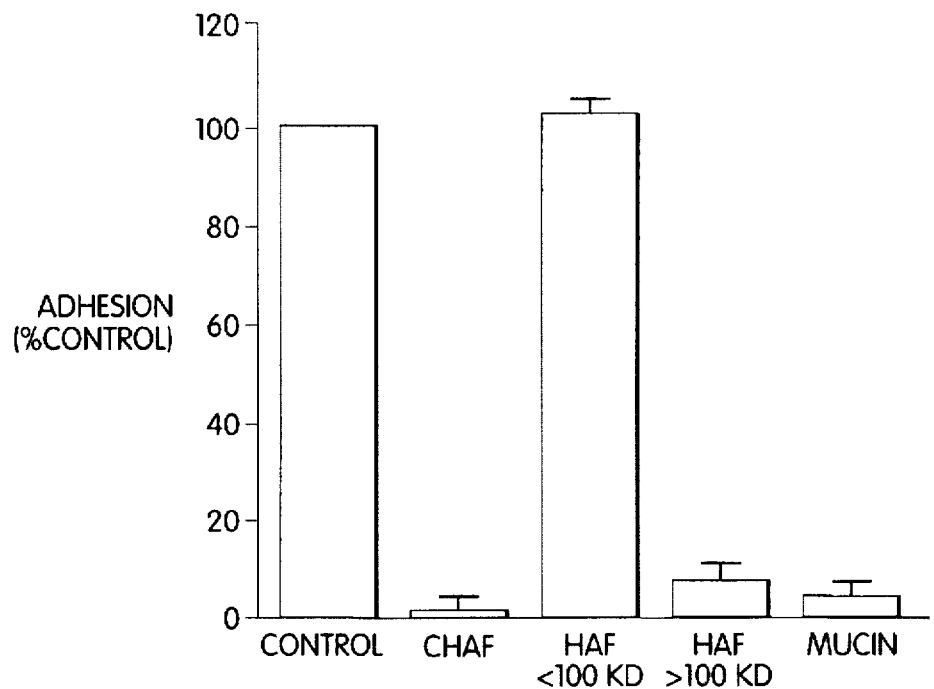
Figure 9:
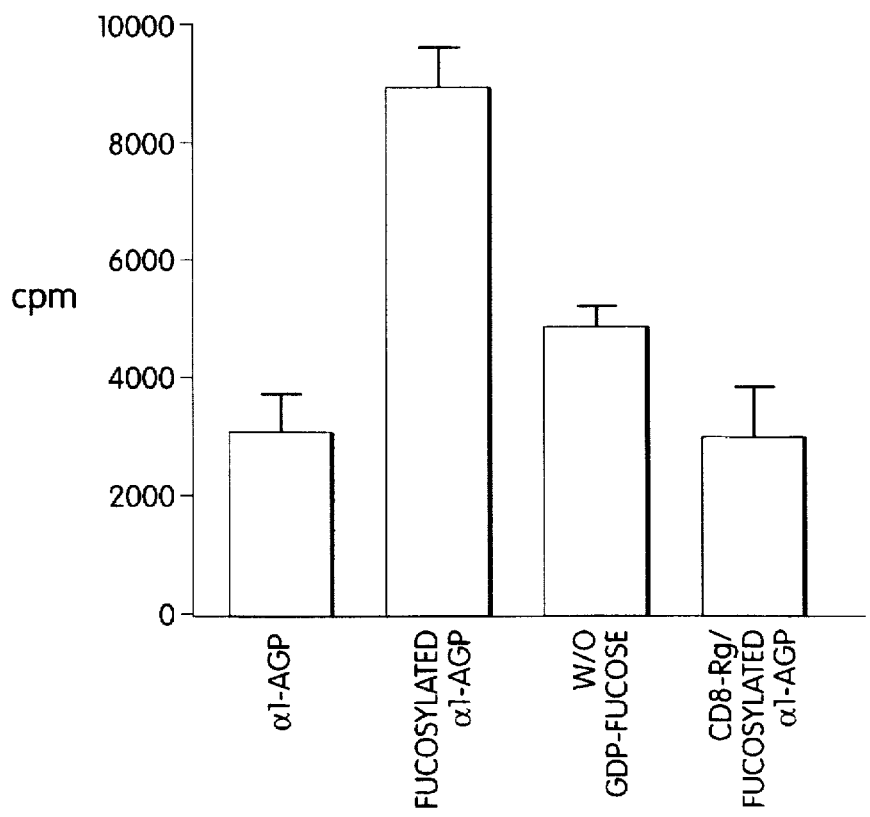
Figure 10:
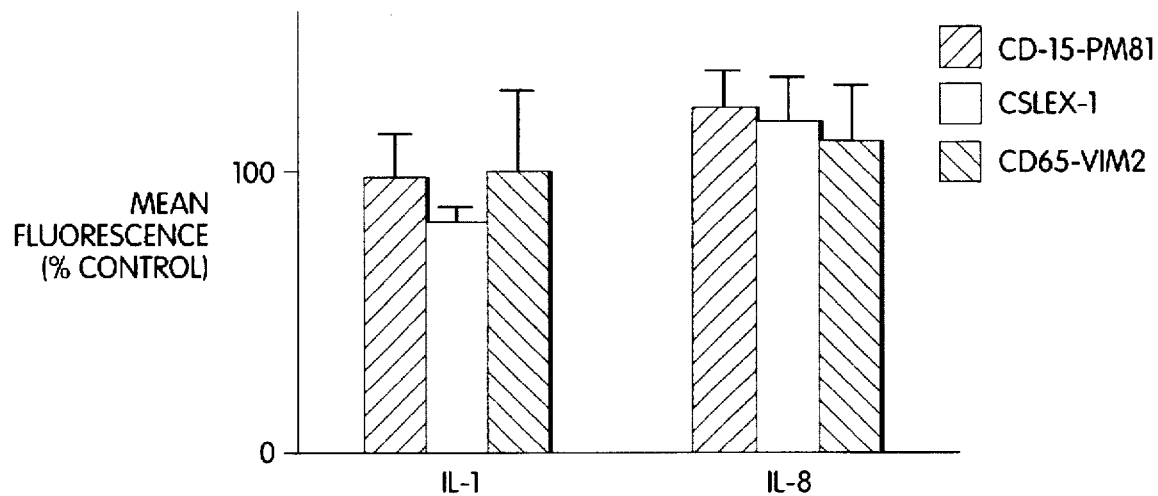
Figure 11:
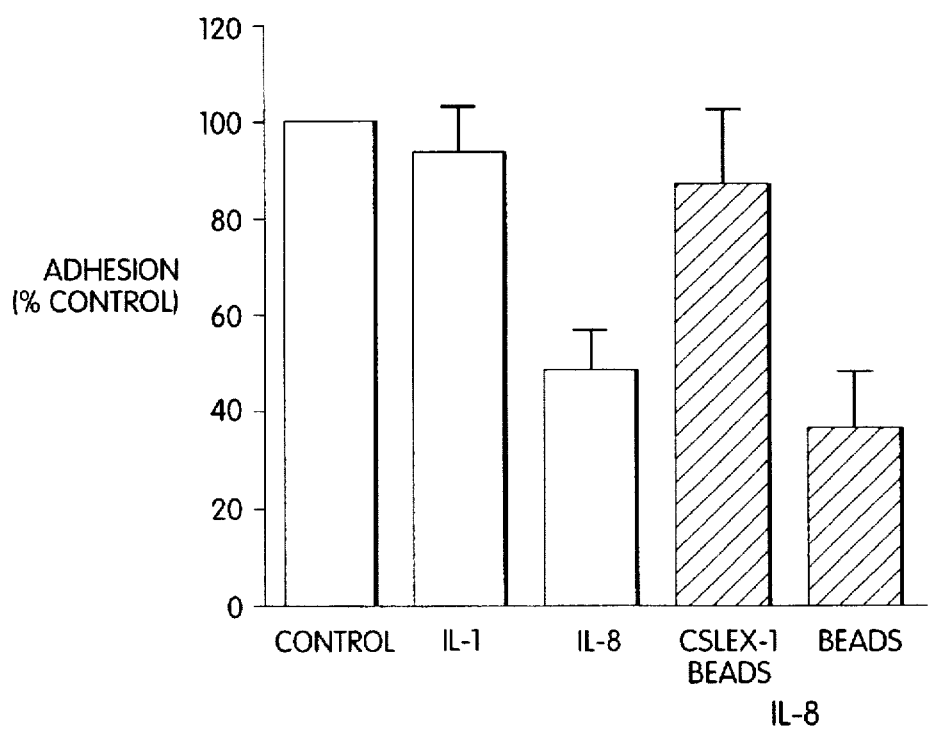

FIGS. 5 A–F is a series of graphs showing the degree of binding of the mammalian cell lines (A) granulocytes, (B) HL-60, (C) THP1, (D) WIDR, (E) U937, and (F) HSB-2 to antibodies directed against the cell surface molecules, CD15, CD63, and sialyl-Le$^x$;

FIG. 6 is a graph showing binding of neuraminidase-treated myeloid cells to ELAM-1 or to α-CD15 antibody;

FIG. 7 is a graph showing inhibition of ELAM-1-bearing cell adhesion by α-sialyl-Le$^x$ antibody;

FIG. 8 is a graph showing the effect of amniotic fluid-derived sialyl-Le$^x$ determinant on binding of myeloid cells to ELAM-1;

FIG. 9 is a graph showing the ability of in vitro-fucosylated α$_1$-acid glycoprotein to bind ELAM-1;

FIG. 10 is a graph showing the effect of IL-1 and IL-8 on cell surface expression of sialyl-Le$^x$; and FIG. 11 is a graph showing the effect of IL-1 and IL-8 on the adhesion of myeloid cells to ELAM-1.

Antibody bearing multiple sialyl-Le$^x$ determinants

In one embodiment, the invention features an antibody bearing one or more carbohydrate side chains which mask the CH2 portion of the immunoglobulin molecule and thus inhibit complement fixation and F$_c$ receptor binding. Such antibodies are useful for disrupting undesirable interactions between cells or proteins, or, generally, for disrupting an interaction between any two molecules, one of which bears a determinant specifically recognized by an antibody. Because the carbohydrate moieties block the immunoglobulin domain which triggers complement fixation and F$_c$ receptor binding, such antibodies do not elicit the undesirable side effects (i.e., those resulting from complement fixation and F$_c$ receptor binding) frequently associated with antibody-based therapies. Preferably, the carbohydrate groups serve not only to inhibit undesirable complement fixation and F$_c$ receptor binding, but also perform the function of competitively inhibiting a carbohydrate ligand-cell adhesion protein interaction. Where the carbohydrate groups perform this function, the antibody generally does not serve any function arising from its specificity, but serves only as a carrier for the carbohydrate groups. There is described below such a molecule, in which the carbohydrate side chain includes the sialyl-Le$^x$ determinant. Sialyl-Le$^x$ normally acts to facilitate interaction between cells which bear it (e.g., neutrophils) and cells which bear the protein, ELAM-1 (e.g., endothelial cells, e.g., those lining the blood vessel walls). Disrupting this interaction has therapeutic applications, for example, in minimizing inflammation, such as that which occurs following tissue injury, e.g., myocardial infarction, or which is characteristic of diseases such as psoriasis or rheumatoid arthritis.

The IgG1 molecule, in its nascent form, bears no sialyl-Le$^x$ side chains. Because N-linked glycan addition sites are well known to be: N X S/T (where N is asparagine, S is serine, T is threonine, and X is any amino acid except proline), we designed a molecule including several such sites for attachment of sialyl-Le$^x$ side chains. Inspection of the IgG1 sequence (FIG. 1, SEQ ID NO:1) reveals at least five sites at which N-linked glycan addition sites may be introduced into the molecule in advantageous locations, where complement fixing and F$_c$ receptor binding ability will be impaired by the process. These sites (i.e., beginning at amino acid residues 274, 287, 295, 322, and 335), although they are preferred sites of N-linked glycan addition are not the only candidates; other useful sites may be identified and incorporated into the IgG1 sequence using, as guidance, the following criteria: (1) The sites are, preferably, located in the CH2 region of the immunoglobulin molecule, i.e., in the portion of the molecule responsible for complement fixation and F$_c$ receptor binding; (2) the sites are located in regions of the sequence, predicted by their hydrophilic nature, to be present on the outside of the immunoglobulin molecule and therefore accessible to the enzymes responsible for attachment of carbohydrate side chains; (3) the sites are located in a region which is minimally disruptive to the primary amino acid sequence and, thus, the predicted secondary amino acid structure. For example, a naturally-occurring site which differs from an N-linked glycan addition site by a single amino acid would be preferable to a site requiring two alterations in the amino acid sequence. Moreover, it is preferable to create an N-linked glycan addition site by subsituting amino acids of similar charge or polarity (e.g., substitution of one uncharged amino acid for another). One or more N-linked glycan addition site substitutions may be engineered into the IgG1-encoding sequence; such sequences (i.e., those which encode an antibody molecule to which sialyl-Le$^x$ moieties are attached) are termed IgG1-sialyl-Le$^x$ or IgG1-Le$^x$.

A particular IgG1 molecule bearing sialyl-Le$^x$ moieties is produced as follows. The IgG1 gene is publically available, and its sequence is shown in FIG. 1 (SEQ.ID NO.:1). The gene is mutagenized by standard methods of in vitro site-directed mutagenesis in order to introduce one or more N-linked glycan addition sites (e.g., those described above and shown above the naturally-occurring sequence in FIG. 1; SEQ ID NO.:2). The gene is then inserted into a vector designed to express the protein in a eukaryotic cell (see, e.g., those vectors described in Gillies et al., U.S. Pat. No. 4,663,281, hereby incorporated by reference). The eukaryotic host cell is preferably a mammalian cell (e.g., a CHO or lec11 cell), and the expression vector containing the mutated IgG1-Le$^x$-encoding sequence is introduced into the host cell by transient or stable transfection using standard techniques. Such host cells are also transfected (transiently or stably) with a vector capable of expressing an α(1,3) fucosyltransferase capable of attaching the sialyl-Le$^x$ groups to the antibody molecule at the glycosylation sites. The α(1,3)fucosyltransferase gene may be expressed from a vector distinct from that encoding IgG1-Le$^x$, or both genes may be carried on, and expressed from, a common vector. Mammalian cells are particularly useful hosts for the synthesis of IgG1-Le$^x$ because they provide all required precursors for sialyl-Le$^x$ production.

An α(1,3)fucosyltransferase cDNA is described in Lowe et al. (*Cell* 63: 475, 1990). The α(1,3)fucosyltransferase enzyme, encoded by this cDNA, recognizes a sialylated precursor molecule and adds either an α(1,3)- or an α(1,4) -linked fucose moiety to N-acetylglucosamine side chains. The sialyl-Le$^x$ determinant is characterized by an α(1,3)-linkage, and, as such, the α(1,3)fucosyltransferase enzyme of Lowe (supra) produces both the desired sialyl-Le$^x$-modified molecules and products bearing α(1,4)-linked fucose which, although not active in binding to ELAM-1, do not interfere with the action of the sialyl-Le$^x$-modified molecules nor produce other undesirable side effects. Production of IgG1-sialyl-Le$^x$ would be more efficient, however, if an α(1,3)fucosyltransferase was utilized which exclusively catalyzed α(1,3) fucose linkages. Such a mammalian enzyme exists, and the cDNA therefor can be isolated as follows. A cDNA library, prepared from mRNA which is isolated from a myeloid cell line (e.g., HL-60), is inserted into a mammalian cell expression vector such as πH3M (see, Simmons et al., *Nature* 331: 624, 1988; Aruffo and Seed, *Proc. Natl. Acad. Sci. USA* 84: 8573, 1987) and transfected into a mammalian cell line, preferably, COS7 cells (as described in Seed and Arruffo, *Proc. Natl. Acad. Sci. USA* 84: 3365, 1987). The proper cDNA clone is isolated by the immunoselection procedure described in Aruffo and Seed, supra; Seed and Aruffo, supra; and U.S. patent application Ser. No. 379,076, now abandoned, hereby incorporated by reference. Transfected cells are harvested and incubated with monoclonal antibodies PM-81 (anti-CD15; Medarex, West Lebanon, N.H.), FMC13 (anti-CD15; Sera-Lab/ Accurate Chemical and Scientific, Westbury, N.Y.), MC-1 (anti-CD15; Sera-Lab. Westbury, N.Y.) and VIM8 (anti-CD65). Following incubation (e.g., for 1 hour), cells are separated from free antibody by centrifugation through a cushion of 2% Ficoll in PBS and allowed to settle on plastic dishes coated with affinity-purified goat antibodies to mouse IgM (as described below). Adherent cells are collected and a Hirt supernatant containing episomal DNA is prepared. The purified Hirt supernantant DNA is transformed (e.g., by electroporation) into *E. coli* (preferably, *E. coli* MC1061/p3) by standard techniques and ampicillin- and tetracycline-resistant colonies selected by standard methods. Antibiotic resistant colonies are then pooled and the plasmids amplified (e.g., following addition of spectinomycin hydrochloride overnight). The resulting culture is converted to spheroplasts and the spheroplasts fused to COS7 cells by standard procedures (see, for example, Seed and Aruffo, supra). Cells are allowed to incubate (preferably, 2 to 3 days) and are exposed to antibodies as described above. Preferably, two rounds of spheroplast fusion and "panning" (i.e., the procedure described above) are performed, and the bacterial cells resulting from the last round of panning are collected, and their plasmid DNA prepared. This cDNA encodes an enzyme, i.e., an α(1,3)fucosyltransferase, which directs the appearance of the desired CD15 and CD65 determinants, i.e., the sialyl-Le$^x$ determinant.

Host cells expressing α(1,3)fucosyltransferase and IgG1-Le$^x$ (and thus producing an IgG1 molecule bearing sialyl-Le$^x$ determinants) are grown by standard methods and the IgG1-Le$^x$ protein is purified from a cell lysate based on its affinity for a Protein A column or any other standard technique of antibody isolation and purification.

Use

For administering such a compound to a patient, the pharmaceutically-pure IgG1-Le$^x$ is suspended in an acceptable carrier, e.g., physiological saline, and is delivered to patients intravenously in a single or in multiple doses. Optimally, a sufficient quantity of IgG1-Le$^x$ is provided to saturate all ELAM-1-binding sites on an endothelial cell. Typically, this may be achieved with doses of 0.1 mg/kg or greater. The preferred dosage is in the range of 0.1–2.0 mg/kg.

Other carrier molecules, for example sialyl-Le$^x$-modified α$_1$-acid glycoprotein (α$_1$-AGP-Le$^x$, described below) would be produced generally as described herein and would be administered intravenously to patients as described above (i.e., preferably, at a dose sufficient to saturate all cellular ELAM-1 binding sites, e.g., at 0.1 mg/kg or greater).

IgG1-sialyl-Le$^x$ or α$_1$-AGP-sialyl-Le$^x$ may be used, in one example, for the treatment of a pateint suffering from a heart attack. Following such a trauma, the endothelial cells lining the blood vessels express ELAM-1 on their surfaces and, without treatment, neutrophils, bearing sialyl-Le$^x$ on their surfaces, bind such ELAM-1-bearing endothelial cells, contributing to inflammation. Treatment with a sialyl-Le$^x$-bearing molecule would attenuate the inflammation by competitively inhibiting the interaction between the invading neutrophils and the blood vessel endothelial cells in the vicinity of the heart. Compounds such as IgG1-sialyl-Le$^x$ or α$_1$-AGP-sialyl-Le$^x$ may also be used, as described above, for the treatment of diseases characterized by chronic inflammatory conditions, e.g., rheumatoid arthritis, psoriasis, or penphigus vulgaris.

Experimental Information

Sialyl-Lewis X (sialyl-Le$^x$) determinants were shown to interact with ELAM-1 and facilitate binding to ELAM-1-bearing endothelial cells by the following experiments. These examples are presented to illustrate, not limit, the invention.

Recognition by ELAM-1 of the Sialyl-Le$^x$ determinant

Figure 2:
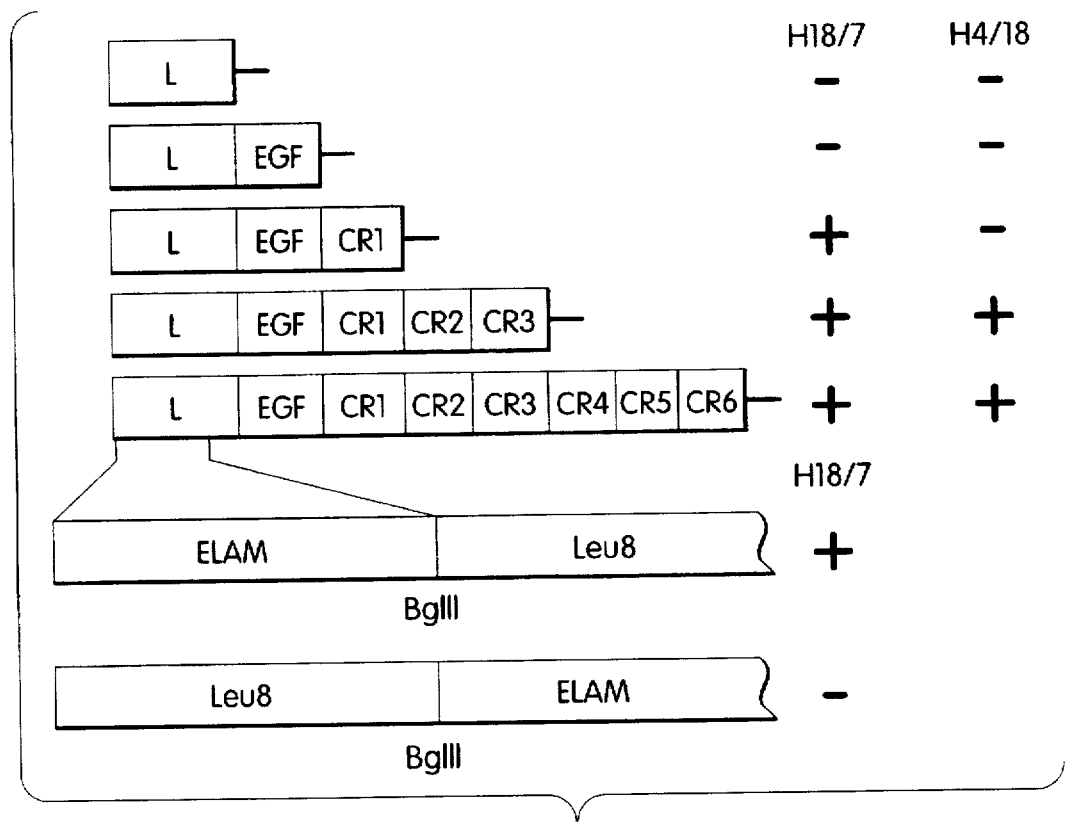
FIG. 2 is a graph showing the binding capability of α-ELAM-1 antibodies to a series of ELAM-1 sub-fragments and ELAM-1 fusion proteins.

The ELAM-1 domains necessary for granulocyte-binding activity were localized using two monoclonal anti-ELAM-1 antibodies: H18/7, which effectively blocks leukocyte adhesion to activated endothelium, and H4/18, which does not (Pober et al., *J. Immunol.* 136: 1680, 1986; Bevilacqua et al., *Proc. Natl. Acad. Sci. USA* 84: 9238, 1987). Full length ELAM-1 was expressed from the cDNA carried on plasmid, pELAM-1 (Bevilacqua et al., *Science* 243: 1160, 1989). Carboxyl terminal deletions of the ELAM-1 cDNA were created by polymerase chain reaction to produce the proteins shown in FIG. 2. Primer sequences for the PCR deletions were designed based on the full-length ELAM-1 sequence of Bevilacqua et al. (*Science* 243: 1160, 1989). Once generated, ELAM-1 cDNA fragments were then fused, by standard techniques, to the transmembrane and intracellular coding portions of a CD7 cDNA (i.e., nucleotides 501 to 1236 of the CD7 cDNA described in Aruffo and Seed, *EMBO. J.* 6: 3313, 1987). Plasmids bearing the resulting fusions were transfected into COS cells. Reactivity to monoclonal antibodies was determined by indirect immunofluorescence microscopy of fixed, permeabilized cells by the method of Aruffo et al., *Cell* 61: 1303, 1990. The results of this analysis are shown in FIG. 2 and are representative of transfections of three to six independent isolates of the constructs shown. FIG. 2 indicates that H18/7 binding required the lectin-related segment plus the EGF-repeat domains, while H4/18 reactivity required, in addition, the first three complement regulatory protein repeat elements. L indicates the lectin-related segment; EGF indicates the EGF-related repeat segment; and CR1–CR6 indicate complement regulatory protein elements.

To further define the binding site for H18/7, a fragment was exchanged between the ELAM-1 cDNA and the equivalent fragment of the related Leu8 (LECCAM-1) cDNA (described in Camerini et al., *Nature* 342: 78, 1989). Leu8 (LECCAM-1)/ELAM-1 chimeras were created by restriction fragment interchange from a conserved BglII site within the lectin domain (i.e., at nucleotide 454 and 475 of the ELAM-1 and Leu8 cDNA sequences, respectively). As shown in FIG. 2, H18/7 bound to an antigenic determinant located principally in the first 75% of the ELAM-1 lectin domain. Together with the above result (i.e., that both the lectin-like and EGF-repeat-like domains were required for H18/7 binding to truncated ELAM-I) suggests that the EGF-related repeat element may play a role in shaping the structure of the lectin domain.

Figure 3:
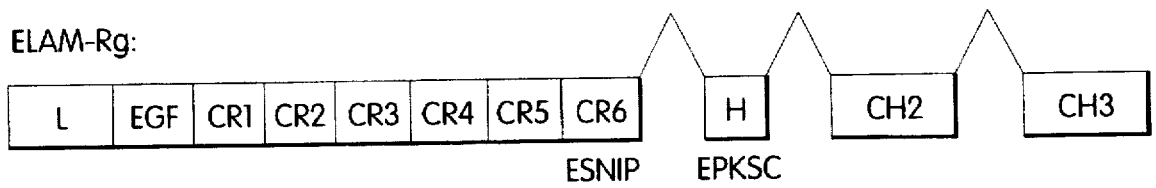
FIG. 3 is a representation of the domain structure of an ELAM-1-IgG1 fusion protein.

To study the possible lectin-carbohydrate interactions suggested by the epitope mapping, a soluble ELAM-1 protein chimera was prepared by the fusion of a cDNA fragment encoding the ELAM-1 extracellular domain to a genomic fragment encoding the hinge, i.e., the CH2 and CH3 domains, of human IgG1 (Aruffo et al., *Cell* 61: 1303, 1990; FIG. 3). The ELAM-1-IgG1 chimera was prepared as follows. Synthetic oligonucleotides having the sequence: CGGAATTCCAGTACTACTCACCTGGTC- CGCCGATGGTCTCCGGGC (SEQ. ID NO.:3) and CCA- GATATACGCGTTGACATTGATTATTGACTAGTTATT (SEQ. ID NO.:4), and corresponding to the splice donor/ carboxyl terminus of ELAM-1 and to a location in the vector upstream of the inserted cDNA, respectively, were prepared by standard techniques. Polymerase chain reaction with these oligonucleotides and the ELAM-1 cDNA expression plasmid, pELAM-1, as template, yielded an 1800 bp fragment which was digested with XhoI and EcoRI and subcloned into XhoI/EcoRI-digested expression vector πH3M (Aruffo and Seed, *Proc. Natl. Acad. Sci. USA* 84: 8573, 1987). The subcloned fragment was released by digestion with XhoI and ScaI and ligated to the XhoI/ScaI-digested IgG1 expression plasmid described in Aruffo et al. *Cell* 61: 1303, 1990. The resulting construct was transfected into COS cells (as described in Seed and Aruffo, *Proc. Natl. Acad. Sci* 84: 3365, 1987), and the desired fusion protein, termed ELAM-Rg, was recovered from the supernatant by adsorption to and elution from protein A-agarose as described in Aruffo et al. (*Cell* 61: 1303, 1990). The initial construct, and a subsequent version in which the majority of the PCR-amplified segment (i.e., nucleotides 1 to 1464 of the ELAM-1 sequence) was replaced by a homologous restriction fragment interchange (to avoid potential mutations introduced during amplification) showed identical binding activity. The soluble protein appeared in the form of disulfide-linked dimers, presumably mediated by the hinge region cysteine residues responsible for the inter-heavy chain linkage of active immunoglobulins.

To determine whether myeloid cells bound soluble ELAM-1, plastic dishes precoated with goat-anti-human IgG antibodies, were incubated with supernatants expressing ELAM-Rg. These experiments were carried out as follows. Human granulocytes were isolated from freshly drawn, heparinized whole blood by centrifugation through Ficoll/ sodium diatrizoate (Mono-Poly Resolving Medium, Flow Laboratories, McLean, Va.) for 20 min. at 800× g. Cell lines were obtained from the American Type Culture Collection (ATCC) and were maintained in IMDM with 10% fetal bovine serum as described in Aruffo and Seed (*Proc. Natl. Acad. Sci. USA* 84: 8573, 1987). Adhesion to ELAM-Rg was carried out in bacterial culture dishes (Falcon 1008, Becton-Dickinson Labware, Lincoln Park, N.J.) to which affinity-purified goat anti-human IgG antibody (Organon Teknika/ Cappel, Malverne Pa.) had been allowed to adsorb at 10 µg/ml in 50 mM Tris-HCl, pH 9.5 for at least one hour. Remaining protein binding sites were then blocked by overnight incubation with 1 mg/ml bovine serum albumin in Phosphate Buffered Saline (PBS; 137 mM NaCl, 2.7 mM KCl, 4.3 mM $Na_2HPO_4.7H_2O$, 1.4 mM $KH_2PO_4$, pH7.3). Dishes were incubated with ELAM-Rg ($\approx$1 µg/ml) for 30 min. at 22°, washed with PBS, overlaid with cells ($10^6$ cells) for 10 min. at 22°, and washed three times with PBS. The adherent cells per unit area of dish were enumerated with the aid of an ocular reticle and scored as follows: >100 cells, +++++; 100–75 cells, ++++; 75–50 cells, +++; 50–25 cells, ++; and 25–10 cells, +. All values represented the average of triplicate determinations.

The treated plastic acquired the ability to specifically bind granulocytes as well as the myeloid cell lines HL60 and THP1 (FIG. 4). Other cell lines of both hematopoietic origin (i.e., U937 and HSB-2) and nonhematopoietic origin (i.e., WIDR) were found to bind to the ELAM-1 coated plastic as well (FIG. 4). Dishes coated with CD8 fusion protein (Aruffo et al., *Cell* 61: 1303, 1990) showed negligible affinity (for granulocytes or any of the cell lines tested (Bevilacqua et al., *Proc. Natl. Acad. Sci. USA* 84: 9238, 1987).

To correlate the binding activity with surface phenotype, various monoclonal antibodies recognizing known granulocyte carbohydrate antigens were screened for reactivity with the above cell types. $5\times10^5$ cells were incubated with the following antibodies (as ascites at 1:250 dilution, or as purified antibody at 4 µg/ml): PM-81 (anti-CD15; Medarex, W. Lebanon, N.H.; Ball et al., *J. Immunol.* 130: 2937, 1983), CSLEX-1 (anti-sialyl-Le$^x$; Fukushima et al., *Cancer Res.* 44: 5279, 1984); or VIM2 (anti-CD65; Macher et al., *J. Biol. Chem.* 263: 10186, 1988), followed by a fluorescein-conjugated goat anti-mouse IgG+IgA+IgM antibody (Organon Teknika/Cappel, Malverne, Pa.).

Results are shown in FIGS. 5A–F. Sparse dots represent the negative control (no primary antibody); dense dots, anti-CD15 mAb; solid line, anti-CD63 mAb; and broken line, anti-sialyl-Le$^x$ mAb. The U937 line used herein lacked sialyl-Le$^x$ determinants, unlike the related U937 cell line tested by Terasaki and coworkers (Fukushima et al., *Cancer Res.* 44: 5279, 1984). An initial survey showed that ELAM-1 adhesion potential correlated with the presence of the CD15 determinant (i.e., Le$^x$, or lacto-N-fucopentaose III; Gooi et al., *Nature* 292: 156, 1981; Huang et al., *Blood* 61: 1020, 1983; Magnan et al., *Arch. Biochem. Biophys.* 233; 501, 1984; Gooi et al., *Eur. J. Immunol.* 13: 306, 1983; Tetteroo et al., *Eur. J. Immunol.* 94: 1089, 1984), but not with the determinants associated with CD17 (lactosyl ceramide; Symington et al., *J. Biol. Chem.* 259: 6008, 1984), CD65 (VI$^3$NeuAcIII$^3$FucnorLcnOse$_6$Cer; Macher et al., *J. Biol. Chem.* 263: 10186, 1988) or sulfatides (Fredman et al., *Biochem. J.* 251: 17, 1988).

To further test the correlation between ELAM-1 adhesion potential and the presence of CD15, cells bearing CD15 were treated with neuraminidase, an enzyme known to cleave terminal sialyl groups. HL60 cells ($10^6$/plate) were incubated in 50 µl of 0.15M NaCl, 4 mM $CaCl_2$, pH 5.5, for 1 hr. at 37° in the presence or absence of 41.5 mU of neuraminidase (from Vibrio cholerae, type II, Sigma, St. Louis, Mo.). Cells were washed three times with PBS and adherence to either ELAM-Rg- or PM-81-coated dishes was scored as described above. Dishes were coated with ELAM-Rg as described above, and with purified PM-81 antibody at 10 µg/ml in 50 mM Tris-HCl pH 9.5. Adherence assays were carried out as described above. Results shown in FIG. 6 are expressed as percent of control and were calculated from the mean ± standard deviation for the average of triplicate determinations in three independent experiments.

FIG. 6 indicates that the correlation of ELAM-1 adhesion potential with the presence of CD15 was imperfect because digestion of the cells with neuraminidase abolished binding to ELAM-1 but increased binding to immobilized anti-CD15 antibodies.

Association with CD15 and sensitivity to neuraminidase suggested that the sialylated form of the CD15 carbohydrate antigen might represent the physiological ELAM-1 ligand. To test this idea, CSLEX1 monoclonal antibody was assayed for its ability to inhibit adhesion of HL60 cells to ELAM-Rg. $10^6$ HL60 cells were incubated with CSLEX1 (1:50 in PBS) for 30 min. on ice, then crosslinked with affinity purified goat anti-mouse IgM antibody (Organon Teknika/Cappel, Malverne, Pa.) at 20 µg/ml in PBS for 30 min., and fixed with 2% formaldehyde in PBS for 20 min. at 22°. Cells were washed three times in PBS/1% glycine and incubated with ELAM-1-Rg-coated dishes as described above. The data (presented as percent of control) in FIG. 7 represents the mean ± standard deviation of triplicate determinations in three independent experiments.

FIG. 7 indicates that there exists a very good correspondence between the surface density of sialyl-Le$^x$ and the rank order of the number of cells bound per unit area of ELAM-Rg coated plastic. In addition, anti-sialyl-Le$^x$ antibody completely inhibited adhesion of myeloid cells to ELAM-1, whereas anti-CD65 and anti-CD15 antibodies had no activity under identical conditions.

The carbohydrate epitope recognized by the CSLEX1 antibody has been reported to be NeuNAcα2-3Galβ1-4 (Fucα1-3)GlcNAcβ1-3Gal, based on motifs common to structurally characterized glycolipids with which the antibody reacts (Fukushima et al., Cancer Res. 44: 5279, 1984). Chemical analysis of the fucosylated lactosaminoglycans of neutrophilic granulocytes has shown that both the Le$^x$ (CD15) and sialyl-Le$^x$ determinants are predominantly represented on tetraantennary asparagine-linked glycans whose individual strands are built up from poly(N-acetyllactosamine) chains bearing variable α(1,3)-linked fucose substitutions (Fukuda et al., J. Biol. Chem. 259: 10925, 1984; Spooncer et al., J. Biol. Chem. 259: 4792, 1984). Serological evidence supports the existence of the sialyl dimeric Le$^x$ determinant on granulocytes as well (Fukushi et al., J. Biol. Chem. 259: 10511, 1984; Fukushi et al., Cancer Res. 45: 3711, 1985). As such, the residue on the reducing side of the sialyl-Le$^x$ group is galactose in all of the granulocyte structures thus far identified. Although antibody CSLEX1 blocks binding, the structure recognized by ELAM-1 might be more complex than the structure recognized by CSLEX1. To establish the minimum glycan structure for ELAM-1 binding, chemically-characterized glycans bearing sialyl-Le$^x$ determinants were evaluated for ELAM-1 recognition.

Amniotic fluid is one source of well defined sialyl-Le$^x$ determinant which is found in a very different context than the granulocyte cell surface. The sialyl-Le$^x$-bearing carbohydrate of amniotic mucins is joined β1-6 to a 3-substituted N-acetylgalactosamine, which in turn is attached directly to the polypeptide backbone through O-linkage to serine or threonine (Hanisch et al., Carbohydr. Res. 178: 29, 1988). Amniotic fluid-derived sialyl-Le$^x$ determinants were tested for their ability to block binding of myeloid cells to immobilized ELAM-1. Human amniotic fluid (HAF) was either used without purification, fractionated by centrifugal ultrafiltration (100 kDal nominal cutoff; Centricon 100, Amicon, Danvers Mass.), or fractionated, following phenol extraction, by size exclusion chromatography (Sephacryl S-300 HR) in 4M guanidinium chloride (by the method of Hanisch et al., Carbohydr. Res. 178: 29, 1988) to yield purified mucins. Such mucins were used at a protein concentration of approximately 150 µg/ml. Binding to ELAM-Rg coated plastic was performed as described above. Results (expressed as percent of control) shown in FIG. 8 are the average of triplicate determinations in two independent experiments.

FIG. 8 indicates that, despite the dissimilarity between the granulocyte glycans and the amniotic fluid mucins, purified amniotic fluid mucins, as well as unfractionated amniotic fluid (which appears to contain all of its activity in the mucin-rich high molecular weight fraction), efficiently blocked binding of myeloid cells to immobilized ELAM-1.

Another source of sialyl-Le$^x$ determinants is fucosylated $\alpha_1$-acid glycoprotein ($\alpha_1$-AGP) (Biou et al., Biochim. Biophys. Acta. 913: 308, 1987; Wieruszeski et al., FEBS Lett. 238: 390, 1988). Chemical analysis of human $\alpha_1$-AGP has shown that fucose is present on a minor fraction of N-linked glycans (Schmid et al., Biochim. Biophys. Acta. 492: 291, 1977; Fournet et al., Biochemistry 17: 5206, 1978), but that the asialo protein at least partially blocks the binding of anti-CD15 antibodies (Gooi et al., Eur. J. Immunol. 13: 306, 1983; Tetteroo et al., Eur. J. Immunol. 14: 1089, 1984). A modest (35±9%) reduction in binding of HL60 cells to ELAM-1 (adsorbed to plastic) was achieved with 200 µg/ml of the protein.

In vitro production of a sialyl-Le$^x$ molecule

To extend these results, enzymatically-fucosylated $\alpha_1$-AGP was prepared in vitro. The biosynthesis of the sialyl-Le$^x$ determinant is controlled by a specific α(1,3) fucosyltransferase (Campbell et al., Cell 35: 303, 1983; Campbell et al., J. Biol. Chem. 259: 11208, 1984), which adds fucose to the N-acetylglucosamine moiety of terminal N-acetyllactosamine or its 3-sialyl adduct; a genetically and biochemically distinct specific α(1,3)fucosyltransferase is known to only add fucose to the asialyl precursor (Prieels et al., Eur. J. Biochem. 130: 347, 1983; Muramatsu et al., Eur. J. Biochem. 157: 71, 1986). A third fucosyltransferase is known to form both α(1,3) and a α(1,4) linkages, apparently to unsialylated substrates (Prieels et al., J. Biol. Chem. 256: 10456, 1981; Lowe et al., infra). Biosynthesis of the sialyl-Le$^x$ determinant proceeds by sequential sialylation followed by fucosylation because α(2,3) sialytransferase cannot recognize the fucosylated terminal N-acetyllactosamine that is CD15 (Holmes et al., J. Biol. Chem. 261: 3737, 1986). $\alpha_1$-acid glycoprotein is a good substrate for the α(1,3) fucosyltransferase of amniotic fluid (e.g., Hanisch et al., Carbohydr. Res. 178: 23, 1988), an enzyme which forms sialyl-Le$^x$ from sialylated and nonsialylated precursors, respectively.

Amniotic fluid fucosyltransferase was isolated by affinity chromatography and evaluated for its ability to convert $\alpha_1$-AGP into an ELAM-1 ligand as follows. α(1,3) fucosyltransferase was isolated from concentrated amniotic fluid by fetuin-agarose chromatography as previously described in Hanisch et al. (Carbohydr. Res. 178: 23, 1988) and Mitsakos et al. (Biol. Chem. Hoppe-Seyler 369: 661, 1988). 0.8 µCi GDP$^{14}$C-fucose (225 Ci/mole) and 100 µg of bovine $\alpha_1$-AGP (Sigma, St. Louis, Mo.) were added to a reaction mix containing 25 mM Tris-HCl pH 7.0, 35 mM MgCl$_2$ and 1 mM ATP in a final volume of 120 µl. The reaction was allowed to proceed for 24 h. at 37°, at which time approximately 10% of the $^{14}$C-labeled fucose had been incorporated into TCA-insoluble material. Unincorporated label was removed by centrifugal ultrafiltration (Centricon 10, Amicon, Danvers, Mass.). 20 µl of a 1:5 dilution of the labelled material, or 10 µl of a 1:5 dilution of a similarly constituted reaction mixture lacking labelled GDP-fucose, was adsorbed to plastic dishes (as described above) or to 96 well microtiter plates (Falcon 3911, Becton Dickinson, Oxnard, Calif.). Wells were incubated at 22° with ELAM-Rg or CDS-Rg at 1 µg/ml for 1 hr., washed with PBS, and incubated with a radioiodinated goat anti-human IgG antibody (DuPont/NEN, Boston, Mass.) for an additional hr. Following washing, labelled antibody binding was measured in a gamma counter. Results shown in FIG. 9 are expressed as the mean ± standard deviation of quadruplicate determinations and are representative of two independent experiments.

FIG. 9 shows that $\alpha_1$-AGP incubated with fucosyltransferase in the presence of GDP-fucose bound significantly more ELAM-Rg than did $\alpha_1$-AGP alone, or $\alpha_1$-AGP incubated with enzyme in the absence of GDP-fucose.

The fucosylated glycans of asialo-$\alpha$-AGP bear the terminal structure Gal$\beta$(1-4)-(Fuc$\alpha$(1-3))GlcNAc$\beta$(1-4)Man, while the nonfucosylated termini of the asialoprotein consist of the N-acetyllactosamine group joined either $\beta$(1-4), $\beta$(1-2), or $\alpha$(1-6) to mannose (Fournet et al., *Biochemistry* 17: 5206, 1978). Hence neither any pre-existing sialyl-Le$^x$ determinants of $\alpha_1$-AGP nor any of the potential fucosyl adducts to N-acetylglucosamine can be joined to galactose. These results, together with the inhibition of ELAM-1 binding by mucin O-linked glycans, indicate that the sialyl-Le$^x$ grouping by itself has appreciable affinity for ELAM-1. It remains to be determined, though, whether quantitatively stronger ELAM-1 binding might be promoted by residues neighboring the sialyl-Le$^x$ determinants on granulocytes or by steric factors affecting their accessibility.

IL-8 blocks myeloid cell adhesion to ELAM-1

It has been reported that the release of IL-8 from IL-1-treated endothelial cells causes granulocytes to lose the ability to bind to IL-1 induced endothelium (Gimbrone et al., *Science* 246: 1601, 1989). The effect of IL-1 and IL-8 on sialyl-Le$^x$ surface antigen expression was determined as follows. Granulocytes were incubated with IL-1$\beta$ (10 ng/ml; Pepro Tech, Rock Hill, N.J.) or IL-8 (25 ng/ml; Pepro Tech, Rock Hill, N.J.) for 20 min. at 37°, washed three times, and incubated with a monoclonal antibody to either CD15 (PM-81), CD65 (VIM2) or sialyl-Le$^x$ (CSLEX1) (described above) on ice. Results in FIG. 10 are given as the relative mean fluorescence intensity (MFI) determined by flow cytometry, as a percent of the MFI of granulocytes incubated in parallel without cytokines, and are representative of four experiments.

FIG. 10 shows that neither IL-1 nor IL-8 caused a substantial reduction in the expression of cell surface sialyl-Le$^x$.

To test the ability of supernatants harvested from granulocytes exposed to IL-8 to block binding to ELAM-1, granulocytes (5×10$^7$/ml) were incubated with IL-1 or IL-8 (at the concentrations above) for 1 hr. at 37°. Supernatants were collected after centrifugation and incubated with ELAM-Rg-coated dishes. Cells were added after 30 min. and binding was determined as described above. Immunoadsorption was performed with 40 μl of Protein-A agarose beads (Sigma, St. Louis, Mo.) to which 10 μg of affinity purified rabbit anti-mouse IgM were adsorbed, followed by 5 μl of CSLEX1 ascites. Control beads were similarly prepared but were not incubated with CSLEX1. The beads were washed with PBS and incubated with the supernatants for 1 hr. at 4°. Results are shown in FIG. 11 and are expressed as the percent of cells bound, relative to the number bound in the presence of supernatants of granulocytes incubated without cytokine under the same conditions. Data shown are mean ± standard deviation of triplicate determinations in three independent experiments.

FIG. 11 shows that supernatants harvested from cultures of granulocytes treated with IL-8, but not IL-1, blocked the adhesion of HL60 cells to immobilized ELAM-1, and the binding inhibition could be specifically reversed by adsorption of the supernatants with solid-phase CSLEX1, but not with the immunoadsorption matrix alone.

OTHER EMBODIMENTS

Other embodiments are within the claims. For example, the invention encompasses any antibody with decreased ability to fix complement and bind an F$_c$ receptor as a result of attached carbohydrate side chains; as described above, these include antibodies useful for their immunologic specificity (e.g., antibodies, e.g., MY904, Todd et al., U.S. Pat. No. 4,840,793) which competitively inhibit cell-cell interactions as well as antibodies which are used only as carriers for therapeutic carbohydrate groups. Because N-linked glycan addition sites are well known to be: Asparagine (N), X, Serine (S) or Threonine (T), where X stands for any residue except proline, one skilled in the art may design a molecule having any number of such sites and thus any number of carbohydrate side chains. Glycosylation sites are incorporated into the antibody sequence, for example, by in vitro site-directed mutagenesis.

Non-complement fixing and non-F$_c$ receptor binding antibodies would be used for purposes other than treating inflammation. For example, such an antibody directed against GPII$_b$III$_a$ may be used to inhibit platelet aggregation and therefore would be useful for the treatment of myocardial infarction. Antibodies to proteins, such as fibrin or one of the clotting cascade proteins, would be useful for inhibiting thrombotic formation. In general, any antibody (including, without limitation, anti-Mo-1 and anti-CD14) proposed or demonstrated to have a therapeutic use may be improved by the addition of carbohydrate moieties which mask the antibody's ability to fix complement and bind an F$_c$ receptor. This characteristic would be particularly important, for example, for immunoglobulin fusion proteins (for example, an $\alpha_1$-AGP-IgG1 fusion protein). In this case, a protein of interest is fused (for example, genetically) to an immunoglobulin molecule to increase the protein's serum half life. Because these fusion proteins have an extended life in the patient, they are more likely to be recognized as foreign antigens, and it is therefore particularly useful for such proteins to evade the patient's F$_c$ receptor binding and complement fixation systems.

For the purpose of blocking interactions between cells or proteins, any other appropriate carrier molecule may be utilized. Generally, proteins are preferred because of their relatively long half-lives in serum. One class of carrier proteins are serum proteins such as albumin (e.g., bovine serum albumin or human serum albumin), transferrin, or α-2 macroglobulin. The carrier proteins can contain endogenous glycan addition sites or sites may be introduced into the DNA sequence of the carrier protein (as described above) by, for example, site-directed mutagenesis. The carrier molecule, less preferably, may be a lipid. In one example, the lipid, with one or more attached carbohydrate moieties (e.g., sialyl-Le$^x$ determinants), is delivered as a liposome to a target cell wall (e.g., an endothelial cell wall). The liposome may block a cell or protein interaction or may be used to deliver a drug to its appropriate site of action.

Cell adhesion molecules in addition to ELAM-1 may be inhibited by attachment of appropriate carbohydrate recognition moieties to a carrier molecule as described above. Such cell adhesion molecules may include, without limitation, LFA-1, LFA-3, ICAM-1, PADGEM, Mel-14, LAM-1, a cadherin, cell-CAM, or an N-CAM. Other glycans may be attached including, without limitation, any N-linked glycan, O-linked glycan, GMP-140, Leu8, and phosphatidyl inositol phosphate glycans. In cases where the glycan addition signal is known, it may be introduced into the DNA sequence of an organic carrier molecule as described above. Alternatively, if the precise site is not known, but the general region of such an addition site in some naturally-occurring molecule has been defined, a DNA fragment (from the sequence encoding the naturally-occurring molecule) which includes that region may be cloned into the DNA sequence of the desired carrier molecule (e.g., an IgG1- or $\alpha_1$-AGP-encoding sequence).

Production of carrier molecules bearing carbohydrate moieties may be carried out in a cell, preferably, a eukaryotic cell other than yeast. Mammalian cells, e.g., mammalian cell lines, provide particularly suitable hosts. These cells generally synthesize the necessary precursor molecules and produce or can be engineered to produce the enzymes responsible for carbohydrate attachment. For the attachment of sialyl-Le$^x$ determinants, mammalian cell lines such as CHO and lec11 are particularly suitable. Alternatively, carbohydrate moieties may be attached to a carrier molecule in vitro, i.e., extracellularly. In one example, α-(1,3) fucosyltransferase would be bound to a solid support (e.g., a column) and the desired carrier molecule passed over the bound fucosyltransferase enzyme, under conditions which facilitate attachment of sialyl-Le$^x$ groups to their appropriate site or the carrier molecule.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2287
        ( B ) TYPE: nucleic acid
        ( C ) STRANDEDNESS: single
        ( D ) TOPOLOGY: linear ( x i ) SEQUENCE DESCRIPTION: SEQUENCE ID NO: 1:

```
AAG  CTT  ACC  ACC  ATG  GAC  TGG  ACC  TGG  AGG  TTC  CTC  TTC  TTT  GTG  GTG        48
Leu  Leu  Thr  Thr  Met  Asp  Trp  Thr  Trp  Arg  Phe  Leu  Phe  Phe  Val  Val
                    5                        10                      15

GCA  GCA  GCT  ACA  GGT  GTC  CAG  TCC  CAG  GTG  CAG  CTG  GTG  CAG  TCT  GGG        96
Ala  Ala  Ala  Thr  Gly  Val  Gln  Ser  Gln  Val  Gln  Leu  Val  Gln  Ser  Gly
               20                       25                      30

GCT  GAG  GTG  AAG  AAG  CCT  GGG  TCC  TCG  GTG  AAG  GTC  TCC  TGC  AAG  GCT       144
Ala  Glu  Val  Lys  Lys  Pro  Gly  Ser  Ser  Val  Lys  Val  Ser  Cys  Lys  Ala
          35                        40                      45

TCT  GGA  GGC  ACC  TTC  AGC  AGC  TAT  GCT  ATC  AGC  TGG  GTG  CGA  CAG  GCC       192
Ser  Gly  Gly  Thr  Phe  Ser  Ser  Tyr  Ala  Ile  Ser  Trp  Val  Arg  Gln  Ala
     50                       55                      60

CCT  GGA  CAA  GGG  CTT  GAG  TGG  ATG  GGA  GGG  ATC  ATC  CCT  ATC  TTT  GGT       240
Pro  Gly  Gln  Gly  Leu  Glu  Trp  Met  Gly  Gly  Ile  Ile  Pro  Ile  Phe  Gly
65                       70                      75                          80

ACA  GCA  AAC  TAC  GCA  CAG  AAG  TTC  CAG  GGC  AGA  GTC  ACG  ATT  ACC  GCG       288
Thr  Ala  Asn  Tyr  Ala  Gln  Lys  Phe  Gln  Gly  Arg  Val  Thr  Ile  Thr  Ala
                    85                       90                      95

GAC  GAA  TCC  ACG                                                                    300
Asp  Glu  Ser  Thr
               100

AGCACAGCCT  ACATGGAGCT  GAGCAGCCTG  AGATCTGAGG  ACACGGCCGT  GTATTACTGT        360

GCG  AGA  GAT  AAT  GGA  GCG  TAT  TGT  AGT  GGT  GGT  AGC  TGC  TAC  TCG  GGC       408
Ala  Arg  Asp  Asn  Gly  Ala  Tyr  Cys  Ser  Gly  Gly  Ser  Cys  Tyr  Ser  Gly
                    105                      110                     115

TGG  TTC  GAC  CCC  TGG  GGC  CAG  GGA  ACC  CTG  GTC  ACC  GTC  TCT  TCA            453
Trp  Phe  Asp  Pro  Trp  Gly  Gln  Gly  Thr  Leu  Val  Thr  Val  Ser  Ser
               120                      125                     130

GGTGAGTACT  GAATTCTAGC  TTTCTGGGGC  AGGCCAGGCC  TGACCTTGGC  TTTGGGGCAG        513

GGAGGGGGCT  AAGGTGAGGC  AGGTGGCGCC  AGCAGGTGCA  CACCCAATGC  CCATGAGCCC        573

AGACACTGGA  CGCTGAACCT  CGCGGACAGT  TAAGAACCCA  GGGGCCTCTG  CGCCTGGGCC        633

CAGCTCTGTC  CCACACCGCG  GTCACATGGC  ACCACCTCTC  TTGCA                         678

GCC  TCC  ACC  AAG  GGC  CCA  TCG  GTC  TTC  CCC  CTG  GCA  CCC  TCC  TCC  AAG       726
Ala  Ser  Thr  Lys  Gly  Pro  Ser  Val  Phe  Pro  Leu  Ala  Pro  Ser  Ser  Lys
               135                      140                     145

AGC  ACC  TCT  GGG  GGC  ACA  GCG  GCC  CTG  GGC  TGC  CTG  GTC  AAG  GAC  TAC       774
```

```
                Ser Thr Ser Gly Gly Thr Ala Ala Leu Gly Cys Leu Val Lys Asp Tyr
                        150                 155                 160

TTC CCC GAA CCG GTG ACG GTG TCG TGG AAC TCA GGC GCC CTG ACC AGC              822
Phe Pro Glu Pro Val Thr Val Ser Trp Asn Ser Gly Ala Leu Thr Ser
        165                 170                 175

GGC GTG CAC ACC TTC CCG GCT GTC CTA CAG TCC TCA GGA CTC TAC TCC              870
Gly Val His Thr Phe Pro Ala Val Leu Gln Ser Ser Gly Leu Tyr Ser
180                 185                 190                 195

CTC AGC AGC GTG GTG ACC GTG CCC TCC AGC AGC                                  903
Leu Ser Ser Val Val Thr Val Pro Ser Ser Ser
                    200             205

TTGGGCACCC AGACCTACAT CTGCAACGTG AATCACAAGC CCAGCAACAC CAAGGTG               960

GAC AAG AAA GTT                                                              972
Asp Lys Lys Val
            210

GGTGAGAGGC CAGCACAGGG AGGGAGGGTG TCTGCTGGAA GCAGGCTCAG CGCTCCTGCC           1032

TGGACGCATC CCGGCTATGC AGCCCCAGTC CAGGGCAGCA AGGCAGGCCC CGTCTGCCTC           1092

TTCACCCGGA GCCTCTGCCC GCCCCACTCA TGCTCAGGGA GAGGGTCTTC TGGCTTTTTC           1152

CCAGGCTCTG GGCAGGCACA GGCTAGGTGC CCCTAACCCA GGCCCTGCAC ACAAAGGGGC           1212

AGGTGCTGGG CTCAGACCTG CCAAGAGCCA TATCCGGGAG GACCCTGCCC CTGACCTAAG           1272

CCCACCCCAA AGGCCAAACT CTCCACTCCC TCAGCTCGGA CACCTTCTCT CCTCCCAGAT           1332

TCCAGTAACT CCCAATCTTC TCTCTGC                                               1359

AGA GCC CAA ATC TTG TGA CAA AAC TCA CAC ATG CCC ACC GTG CCC                 1404
Glu Pro Lys Ser Cys Asp Lys Thr His Thr Cys Pro Pro Cys Pro
            215                 220                 225

AGGTAAGCCA GCCCAGGCCT CGCCCTCCAG CTCAAGGCGG GACAGGTGCC CTAGAGTAGC           1464

CTGCATCCAG GGACAGGCCC CAGCCGGGTG CTGACACGTC CACCTCCATC TCTTCCTCA            1523

GCA CCT GAA CTC CTG GGG GGA CCG TCA GTC TTC CTC TAG GGG GGT TTT             1571
Ala Pro Glu Leu Leu Gly Gly Pro Ser Val Phe Leu Phe Pro Pro Lys
                230                 235                 240

GGG TTC CTG TGG GAG TAC TAG AGG GCC TGG GGA CTC CAG TGT ACG CAC             1619
Pro Lys Asp Thr Leu Met Ile Ser Arg Thr Pro Glu Val Thr Cys Val
                245                 250                 255

CTG GTG GAC GTG AGC CAC GAA GAC CCT GAG GTC AAG TTC AAC TGG TAC             1667
Val Val Asp Val Ser His Glu Asp Pro Glu Val Lys Phe Asn Trp Tyr
            260                 265                 270

GTG GAC GGC GTG GAG GTG CAT AAT GCC AAG ACA AAG CCG CGG GAG GAG             1715
Val Asp Gly Val Glu Val His Asn Ala Lys Thr Lys Pro Arg Glu Glu
        275                 280                 285

CAG TAC AAC AGC ACG TAC CGG GTG GTC AGC GTC CTC ACC GTC CTG CAC             1763
Gln Tyr Asn Ser Thr Tyr Arg Val Val Ser Val Leu Thr Val Leu His
290                 295                 300                 305

CAG GAC TGG CTG AAT GGC AAG GAG TAC AAG TGC AAG GTC TCC AAC AAA             1811
Gln Asp Trp Leu Asn Gly Lys Glu Tyr Lys Cys Lys Val Ser Asn Lys
            310                 315                 320

GCC CTC CCA GCC CCC ATC GAG AAA ACC ATC TCC AAA GCC AAA                     1853
Ala Leu Pro Ala Pro Ile Glu Lys Thr Ile Ser Lys Ala Lys
                325                 330             335

GGTGGGACCC GTGGGGTGCG AGGGCCACAT GGACAGAGGC CGGCTCGGCC CACCCTCT            1911

GCCCTGAGAG TGACCGCTGT ACCAACCTCT GTCCTACA                                   1949

GGG CAG CCC CGA GAA CCA CAG GTG TAC ACC CTG CCC CCA TCC CGG GAT             1997
Gly Gln Pro Arg Glu Pro Gln Val Tyr Thr Leu Pro Pro Ser Arg Asp
                340                 345                 350

GAG CTG ACC AAG AAC CAG GTC AGC CTG ACC TGC CTG GTC AAA GGC TTC             2045
```

| | | | | | | | | | | | | | | |
|---|---|---|---|---|---|---|---|---|---|---|---|---|---|---|
| Glu | Leu | Thr | Lys<br>355 | Asn | Gln | Val | Ser | Leu<br>360 | Thr | Cys | Leu | Val | Lys<br>365 | Gly Phe |

```
TAT CCC AGC GAC ATC GCC GTG GAG TGG GAG AGC AAT GGG CAG CCG GAG         2093
Tyr Pro Ser Asp Ile Ala Val Glu Trp Glu Ser Asn Gly Gln Pro Glu
        370             375             380

AAC AAC TAC AAG ACC ACG CCT CCC GTG CTG GAC TCC GAC GGC TCC TTC         2141
Asn Asn Tyr Lys Thr Thr Pro Pro Val Leu Asp Ser Asp Gly Ser Phe
385             390             395

TTC CTC TAC AGC AAG CTC ACC GTG GAC AAG AGC AGG TGG CAG CAG GGG         2189
Phe Leu Tyr Ser Lys Leu Thr Val Asp Lys Ser Arg Trp Gln Gln Gly
400             405             410             415

AAC GTC TTC TCA TGC TCC GTG ATG CAT GAG GCT CTG CAC AAC CAC TAC         2237
Asn Val Phe Ser Cys Ser Val Met His Glu Ala Leu His Asn His Tyr
            420             425             430

ACG CAG AAG AGC CTC TCC CTG TCT CCG GGT AAA                             2270
Thr Gln Lys Ser Leu Ser Leu Ser Pro Gly Lys
            435             440

TGAGTGCGAC GGCCGGC                                                      2287
```

(2) INFORMATION FOR SEQ ID NO:2:

(i) SEQUENCE CHARACTERISTICS:
      (A) LENGTH: 442
      (B) TYPE: amino acid
      (C) STRANDEDNESS:
      (D) TOPOLOGY: linear (xi) SEQUENCE DESCRIPTION: SEQUENCE ID NO: 2:

```
Leu Leu Thr Thr Met Asp Trp Thr Trp Arg Phe Leu Phe Val Val
                5               10              15

Ala Ala Ala Thr Gly Val Gln Ser Gln Val Gln Leu Val Gln Ser Gly
            20              25              30

Ala Glu Val Lys Lys Pro Gly Ser Ser Val Lys Val Ser Cys Lys Ala
            35              40              45

Ser Gly Gly Thr Phe Ser Ser Tyr Ala Ile Ser Trp Val Arg Gln Ala
    50              55              60

Pro Gly Gln Gly Leu Glu Trp Met Gly Gly Ile Ile Pro Ile Phe Gly
65              70              75              80

Thr Ala Asn Tyr Ala Gln Lys Phe Gln Gly Arg Val Thr Ile Thr Ala
            85              90              95

Asp Glu Ser Thr Ala Arg Asp Asn Gly Ala Tyr Cys Ser Gly Gly Ser
            100             105             110

Cys Tyr Ser Gly Trp Phe Asp Pro Trp Gly Gln Gly Thr Leu Val Thr
            115             120             125

Val Ser Ser Ala Ser Thr Lys Gly Pro Ser Val Phe Pro Leu Ala Pro
130             135             140

Ser Ser Lys Ser Thr Ser Gly Gly Thr Ala Ala Leu Gly Cys Leu Val
145             150             155             160

Lys Asp Tyr Phe Pro Glu Pro Val Thr Val Ser Trp Asn Ser Gly Ala
                165             170             175

Leu Thr Ser Gly Val His Thr Phe Pro Ala Val Leu Gln Ser Ser Gly
            180             185             190

Leu Tyr Ser Leu Ser Ser Val Val Thr Val Pro Ser Ser Ser Asp Lys
            195             200             205

Lys Val Glu Pro Lys Ser Cys Asp Lys Thr His Thr Cys Pro Pro Cys
            210             215             220

Pro Ala Pro Glu Leu Leu Gly Gly Pro Ser Val Phe Leu Phe Pro Pro
225             230             235             240
```

| | | | | | | | | | | | | | | |
|---|---|---|---|---|---|---|---|---|---|---|---|---|---|---|
| Lys | Pro | Lys | Asp | Thr 245 | Leu | Met | Ile | Ser | Arg 250 | Thr | Pro | Glu | Val 255 | Cys |
| Val | Val | Val | Asp 260 | Val | Ser | His | Glu | Asp 265 | Pro | Glu | Val | Asn | Phe 270 | Ser | Trp |
| Tyr | Val | Asp 275 | Gly | Val | Glu | Val | His 280 | Asn | Asn | Lys | Thr | Lys 285 | Pro | Arg | Glu |
| Glu | Asn 290 | Tyr | Ser | Ser | Thr | Tyr 295 | Arg | Val | Val | Ser | Val 300 | Leu | Thr | Val | Leu |
| His 305 | Gln | Asp | Trp | Leu | Asn 310 | Gly | Lys | Glu | Tyr | Lys 315 | Cys | Asn | Val | Ser | Asn 320 |
| Lys | Ala | Leu | Pro | Ala 325 | Pro | Ile | Glu | Lys | Asn 330 | Ile | Ser | Lys | Ala | Lys 335 | Gly |
| Gln | Pro | Arg | Glu 340 | Pro | Gln | Val | Tyr | Thr 345 | Leu | Pro | Pro | Ser | Arg 350 | Asp | Glu |
| Leu | Thr | Lys 355 | Asn | Gln | Val | Ser | Leu 360 | Thr | Cys | Leu | Val | Lys 365 | Gly | Phe | Tyr |
| Pro | Ser 370 | Asp | Ile | Ala | Val | Glu 375 | Trp | Glu | Ser | Asn | Gly 380 | Gln | Pro | Glu | Asn |
| Asn 385 | Tyr | Lys | Thr | Thr | Pro 390 | Pro | Val | Leu | Asp | Ser 395 | Asp | Gly | Ser | Phe | Phe 400 |
| Leu | Tyr | Ser | Lys | Leu 405 | Thr | Val | Asp | Lys | Ser 410 | Arg | Trp | Gln | Gln | Gly 415 | Asn |
| Val | Phe | Ser | Cys 420 | Ser | Val | Met | His | Glu 425 | Ala | Leu | His | Asn | His 430 | Tyr | Thr |
| Gln | Lys | Ser 435 | Leu | Ser | Leu | Ser | Pro 440 | Gly | Lys | | | | | | |

( 2 ) INFORMATION FOR SEQ ID NO:3:

( i ) SEQUENCE CHARACTERISTICS:
    ( A ) LENGTH: 45
    ( B ) TYPE: nucleic acid
    ( C ) STRANDEDNESS: single
    ( D ) TOPOLOGY: linear ( x i ) SEQUENCE DESCRIPTION: SEQUENCE ID NO: 3:

CGGAATTCCA GTACTACTCA CCTGGTCCGC CGATGGTCTC CGGGC    45

( 2 ) INFORMATION FOR SEQ ID NO:4:

( i ) SEQUENCE CHARACTERISTICS:
    ( A ) LENGTH: 39
    ( B ) TYPE: nucleic acid
    ( C ) STRANDEDNESS: single
    ( D ) TOPOLOGY: linear ( x i ) SEQUENCE DESCRIPTION: SEQUENCE ID NO: 4:

CCAGATATAC GCGTTGACAT TGATTATTGA CTAGTTATT    39

We claim:

1. An antibody molecule which comprises at least one sialyl-Le$^x$ determinant, the presence of said sialyl-Le$^x$ determinant interfering with said antibody's ability to fix complement and bind an $F_c$ receptor.

2. The antibody molecule of claim 1, wherein said antibody is IgG1.

3. The antibody molecule of claim 1, wherein said antibody molecule bears multiple said sialyl-Le$^x$ determinants.

4. The antibody of claim 1, wherein said sialyl-Le$^x$ determinant is N-linked.

5. The antibody of claim 1, wherein said antibody is part of an antibody fusion protein.

* * * * *

UNITED STATES PATENT AND TRADEMARK OFFICE
CERTIFICATE OF CORRECTION

PATENT NO. : 5,723,583
DATED : March 3, 1998
INVENTORS : Brian Seed and Gerd Walz It is certified that error appears in the above-identified patent and that said Letters Patent is hereby corrected as shown below:

Col. 6, line 26, replace "penphigus" with --pemphigus--.

Signed and Sealed this

Second Day of May, 2000

Attest:

Q. TODD DICKINSON

*Attesting Officer*  *Director of Patents and Trademarks*